(12) United States Patent
Onarheim

(10) Patent No.: US 12,151,095 B2
(45) Date of Patent: Nov. 26, 2024

(54) SYSTEMS AND METHODS FOR A TRANSCRANIAL ELECTRICAL STIMULATION DEVICE

(71) Applicant: RPW Technology, LLC, Ossining, NY (US)

(72) Inventor: Balder Haraldsøn Onarheim, Copenhagen (DK)

(73) Assignee: RPW Technology, LLC, Ossining, NY (US)

( * ) Notice: Subject to any disclaimer, the term of this patent is extended or adjusted under 35 U.S.C. 154(b) by 341 days.

(21) Appl. No.: 17/712,655

(22) Filed: Apr. 4, 2022

(65) Prior Publication Data

US 2022/0218981 A1 Jul. 14, 2022

Related U.S. Application Data

(63) Continuation of application No. 17/259,506, filed as application No. PCT/US2020/032177 on May 8, 2020, now Pat. No. 11,291,829.

(60) Provisional application No. 62/845,834, filed on May 9, 2019.

(51) Int. Cl.
  *A61N 1/04* (2006.01)
  *A61N 1/08* (2006.01)
(52) U.S. Cl.
  CPC ............. *A61N 1/0456* (2013.01); *A61N 1/08* (2013.01)
(58) Field of Classification Search
  None
  See application file for complete search history.

(56) References Cited

U.S. PATENT DOCUMENTS

| | | |
|---|---|---|
| 2014/0148872 A1 | 5/2014 | Goldwasser et al. |
| 2015/0374971 A1 | 12/2015 | Dar et al. |
| 2017/0113033 A1 | 4/2017 | Wingeier et al. |
| 2017/0197081 A1* | 7/2017 | Charlesworth .... A61N 1/36034 |
| 2017/0224978 A1 | 8/2017 | Lee |
| 2017/0224990 A1* | 8/2017 | Goldwasser ......... A61N 1/0476 |

FOREIGN PATENT DOCUMENTS

| | | |
|---|---|---|
| WO | WO-2009/137683 A2 | 11/2009 |
| WO | WO-2018/141389 A1 | 8/2018 |

OTHER PUBLICATIONS

International Search Report and Written Opinion on PCT Patent Application No. PCT/US2020/032177 dated Sep. 28, 2020 (11 pages).
Notice of Allowance on U.S. Appl. No. 17/259,506 DTD Dec. 9, 2021.

* cited by examiner

*Primary Examiner* — Michael W Kahelin
(74) *Attorney, Agent, or Firm* — Foley & Lardner LLP

(57) ABSTRACT

A transcranial electrical stimulation device includes a base, a first electrode, and a second electrode. The base includes a center portion, a first end portion, a second end portion, and a first surface. The first end portion and the second end portion are angled relative to the center portion. The first electrode includes a first conductive cup and a first post. The second electrode includes a second conductive cup and a second post.

8 Claims, 18 Drawing Sheets

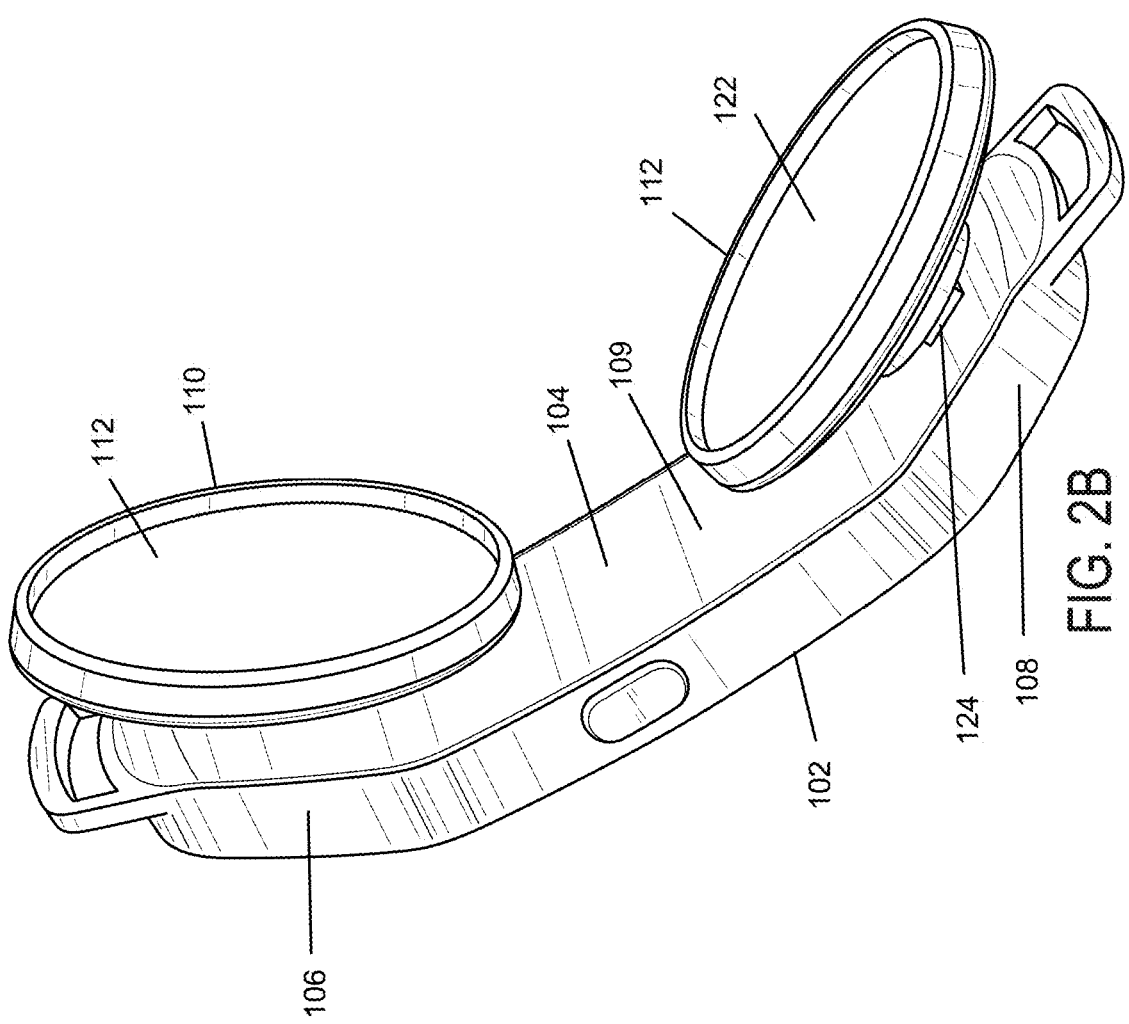

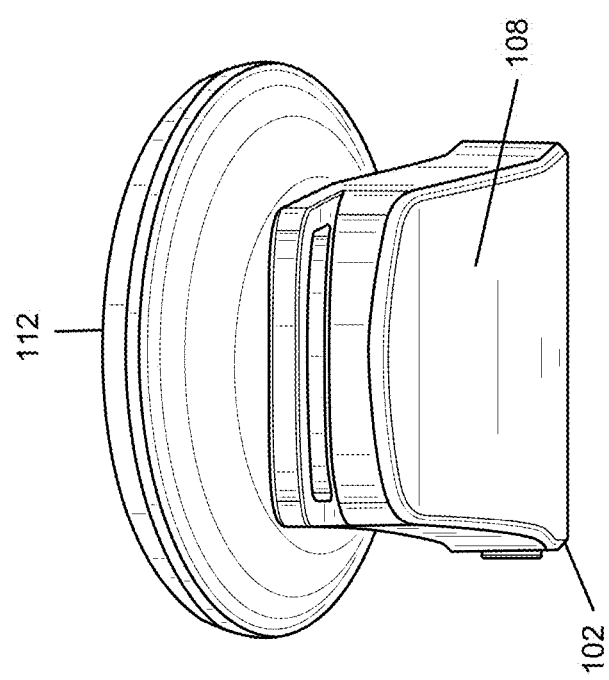

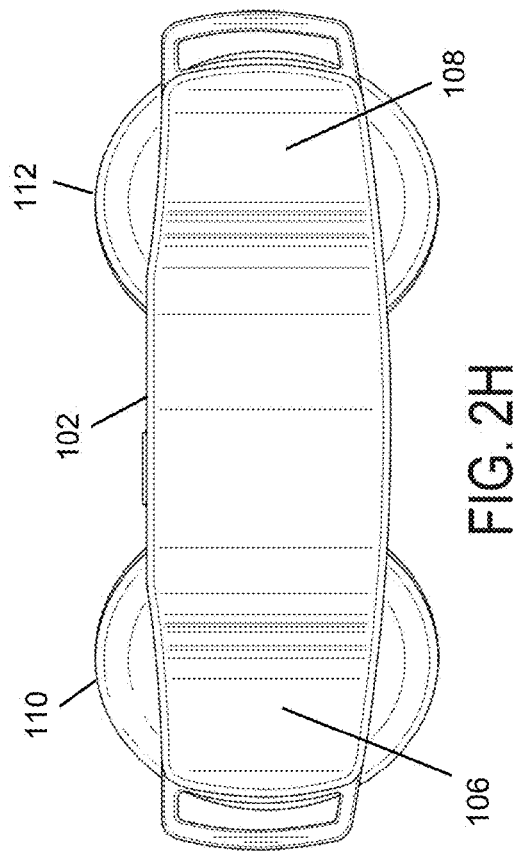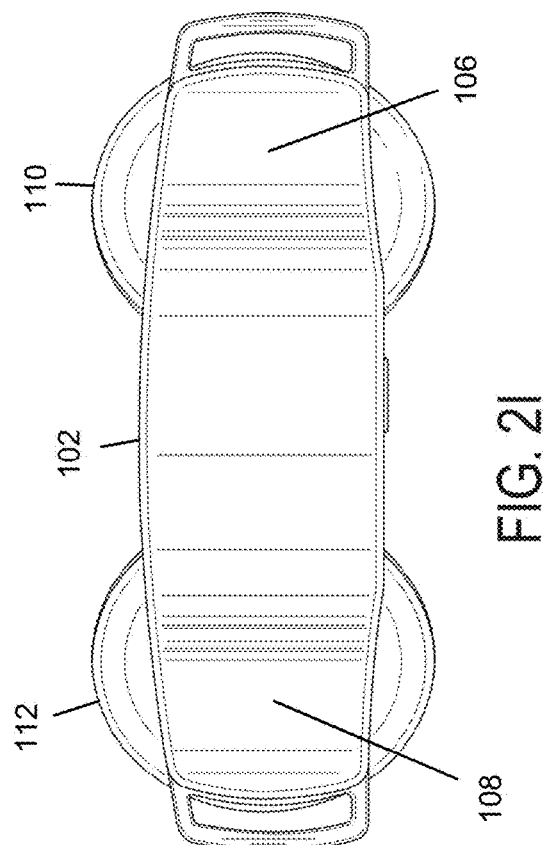

SYSTEMS AND METHODS FOR A TRANSCRANIAL ELECTRICAL STIMULATION DEVICE

RELATED APPLICATIONS

This application is a continuation of U.S. patent application Ser. No. 17/259,506, filed Jan. 1, 2021 (now U.S. Pat. No. 11,291,829), which is a national stage application of International Application No. PCT/US2020/0321775, filed May 8, 2020, which claims the benefit of and priority to U.S. Provisional Patent Application No. 62/845,834, filed May 9, 2019, the entire contents of which are incorporated herein by reference.

TECHNICAL FIELD

The present disclosure generally relates to the field of transcranial electrical stimulation, and more specifically to systems and methods of transcranial electrical stimulation devices.

BACKGROUND

Transcranial direct current stimulation (tDCS), a type of non-invasive neurostimulation, can deliver a low level of current to the brain through electrodes placed on a head. The level of current delivered by tDCS can facilitate the hyperpolarization or depolarization of neurons in the brain. A tDCS device can be a portable device that implements transcranial direct current stimulation to a head of a user. However, tDCS devices can suffer from issues relating to bulky components and lack of adaptability with various head sizes of different users.

SUMMARY

The systems and methods of the present disclosure relate to a compact and lightweight transcranial electrical stimulation device which can adapt to head sizes of different users. According to an aspect of the present disclosure, the transcranial electrical stimulation device includes a base. The base includes a center portion, a first end portion, a second end portion, and a first surface extending along the first end portion, the center portion, and the second end portion. The first end portion is connected to the center portion. The first end portion is angled relative to the center portion. The second end portion is opposite the first end portion and connected to the center portion. The second end portion is angled relative to the center portion. The first surface extends along the first end portion, the center portion, and the second end portion. The transcranial electrical stimulation device includes a first electrode attached to the first end portion and on the first surface. The first electrode includes a first conductive cup. The first electrode includes a first post attached to the first conductive cup and the first end portion. The first post includes a flexible material to allow the first conductive cup to bend about the first post. The transcranial electrical stimulation device includes a second electrode attached to the second end portion and on the first surface. The second electrode includes a second conductive cup. The second electrode includes a second post attached to the first conductive cup and the second end portion. The second post includes a flexible material to allow the second conductive cup to bend about the second post.

In some embodiments, the first post spaces the first conductive cup from the first surface by a clearance distance, the clearance distance greater than or equal to 0.25 centimeters and less than or equal to 2 centimeters.

In some embodiments, the first post spaces the first conductive cup from the first surface by a clearance distance, a ratio of the clearance distance to a thickness of the base is greater than or equal to 0.2 to 1 and less than or equal to 1.2 to 1.

In some embodiments, a first diameter of the first conductive cup is greater than a first width of the first end portion. A second diameter of the second conductive cup can be greater than a second width of the second end portion.

In some embodiments, the first conductive cup and the second conductive cup contour to a head of a user.

In some embodiments, the transcranial electrical stimulation device includes a strap extending from the first end portion to the second end portion. The strap can be configured to secure the first electrode and the second electrode to a head of a user. The strap can be adjustable.

In some embodiments, the transcranial electrical stimulation device includes a pin coupled with the first post, and a pin receiver coupled with the first end portion, the pin receiver configured to receive the pin to secure a conductive portion of the first conductive cup to a non-conductive portion of the first conductive cup, the conductive portion coupled with the first post.

In some embodiments, the pin receives current from a power supply and provides the current to the conductive portion of the first conductive cup.

In some embodiments, the transcranial electrical stimulation device includes a charging port disposed on the first surface of the base and on the center portion of the base.

In some embodiments, the transcranial electrical stimulation device includes a second surface of the base extending along the first end portion, the center portion, and the second end portion. The transcranial electrical stimulation device can include a power button disposed on the second surface and on the center portion of the base.

In some embodiments, the transcranial electrical stimulation device includes a second surface of the base extending along the first end portion, the center portion, and the second end portion. The transcranial electrical stimulation device can include a light emitting diode ("LED") disposed on the second surface and on the center portion of the base.

In some embodiments, the first electrode is removably attached to the first end portion. The second electrode can be removably attached to the second end portion.

In some embodiments, the first conductive cup comprises a first raised edge and the second conductive cup comprises a second raised edge.

In some embodiments, a method for engaging in transcranial electrical stimulation includes securing a transcranial electrical stimulation device to a head of a user. The method can include initiating, by a control circuit, a stimulation session wherein the control circuit couples a power supply to a first electrode and a second electrode to enter a powered state. The method can include increasing, by the control circuit, a current to a first current level over a first period of time, wherein the current flows through the head of the user from a first electrode of the transcranial electrical stimulation device to a second electrode of the transcranial electrical stimulation device. The method can include maintaining, by the control circuit, the current at the first current level over a second period of time. The method can include decreasing, by the control circuit, responsive to a termination condition, the current to second current level over a third period of time. The method can include terminating, by the control circuit, the stimulation session wherein the control circuit decouples the power supply to the first electrode and the second electrode to exit the powered state.

In some embodiments, the transcranial electrical stimulation device comprises a LED. The method can include confirming, by the LED through visual cues, that the transcranial electrical stimulation device is properly secured to the head of the user. Initiating the stimulation session can occur responsive to a confirmation that the transcranial electrical stimulation device is properly secured.

In some embodiments, the transcranial electrical stimulation device comprises a LED. The method can include confirming, by the LED through visual cues, that the transcranial electrical stimulation device is improperly secured to the head of the user. The method can include terminating the stimulation session. Terminating the stimulation session can include stopping a flow of current through the head of the user from the first electrode of the transcranial electrical stimulation device to the second electrode of the transcranial electrical stimulation device. Terminating the stimulation session can include exiting the powered state.

In some embodiments, the transcranial electrical stimulation device comprises a power button. The method includes initiating, by activating a power button, the stimulation session wherein the control circuit couples the power supply to the first electrode and the second electrode to enter the powered state. The method includes terminating, by activating a power button, the stimulation session wherein the control circuit decouples the power supply to the first electrode and the second electrode to exit the powered state.

In some embodiments, the termination condition is a predetermined length of time. The termination condition can be an interrupted stimulation session. The termination condition can be a resistance exceeding a threshold.

In some embodiments, the method can include signaling, by an audio component, an operational state of the transcranial electrical stimulation device. The method can include signaling, by a LED, an operational state of the transcranial electrical stimulation device.

In some embodiments, securing the transcranial electrical stimulation device to the head of the user includes adjusting a first position of the first electrode of the transcranial electrical stimulation device and a second position of the second electrode of the transcranial electrical stimulation device.

In some embodiments, a method for engaging in transcranial electrical stimulation comprising securing a transcranial electrical stimulation device to a head of a user in a first orientation such that a first electrode is electrically coupled and positioned proximate to a first surface region of the head and a second electrode is electrically coupled and positioned proximate to a second surface region of the head. The method includes initiating, via a control circuit, a stimulation session. The control circuit couples a power supply to the first electrode and the second electrode to enter a first powered state, increases a current to a first current level over a first period of time, wherein the current flows from the first electrode through the head of the user in a first direction to the second electrode, maintains the current at the first current level over a second period of time, decreases, responsive to a termination condition, the current to a second current level over a third period of time, and terminates the stimulation session wherein the control circuit decouples the power supply to the first electrode and the second electrode to exit the powered state. The method also includes removing the transcranial electrical stimulation device from the head of the user. The method further includes securing the transcranial electrical stimulation device to the head of the user in a second orientation such that the first electrode is electrically coupled and positioned proximate to the second surface region of the head and the second electrode is electrically coupled and positioned proximate to the first surface region of the head and initiating, via the control circuit, a second stimulation session. The control circuit couples the power supply to the first electrode and the second electrode to enter a second powered state, increases the current to the first current level over a third period of time, wherein the current flows from the first electrode through the head of the user in a second direction to the second electrode, maintains the current at the first current level over a fourth period of time, and decreases, responsive to a termination condition, the current to the second current level over a fifth period of time, and terminates the stimulation session, wherein the control circuit decouples the power supply to the first electrode and the second electrode to exit the powered state. The method further includes removing the transcranial electrical stimulation device from the head of the user.

Some or all of the systems, components, and subcomponents of the present disclosure can be single-use or disposable. Also some or all of the systems, components, and subcomponents of the present disclosure can be made of a unitary construction (formed from a single piece of metal, plastic, or other material) or unitary modular construction (plurality of components and/or subcomponents permanently connected by standard means, such as welding or soldering), or of modular construction (plurality of components and/or subcomponents removably connected by standard means, such as threading or snap-fitting).

These and other features of various embodiments can be understood from a review of the following detailed description in conjunction with the accompanying drawings.

It is to be understood that both the foregoing general description and the following detailed description are explanatory and are not restrictive of the present disclosure, as claimed.

BRIEF DESCRIPTION OF THE DRAWINGS

FIG. 2B is a perspective view of the transcranial electrical stimulation device shown in FIG. 2A.

FIG. 2F is a right side view of the transcranial electrical stimulation device shown in FIG. 2A.

FIG. 2H is a top view of the transcranial electrical stimulation device shown in FIG. 2A in a first orientation.

FIG. 2I is a top view of the transcranial electrical stimulation device shown in FIG. 2A in a second orientation.

DETAILED DESCRIPTION

The following detailed description and the appended drawings describe and illustrate various transcranial electrical stimulation device systems and methods. The description and drawings are provided to enable one of skill in the art to make and use one or more transcranial electrical stimulation device systems and/or practice one or more methods. They are not intended to limit the scope of the claims in any manner.

Figure 2A:
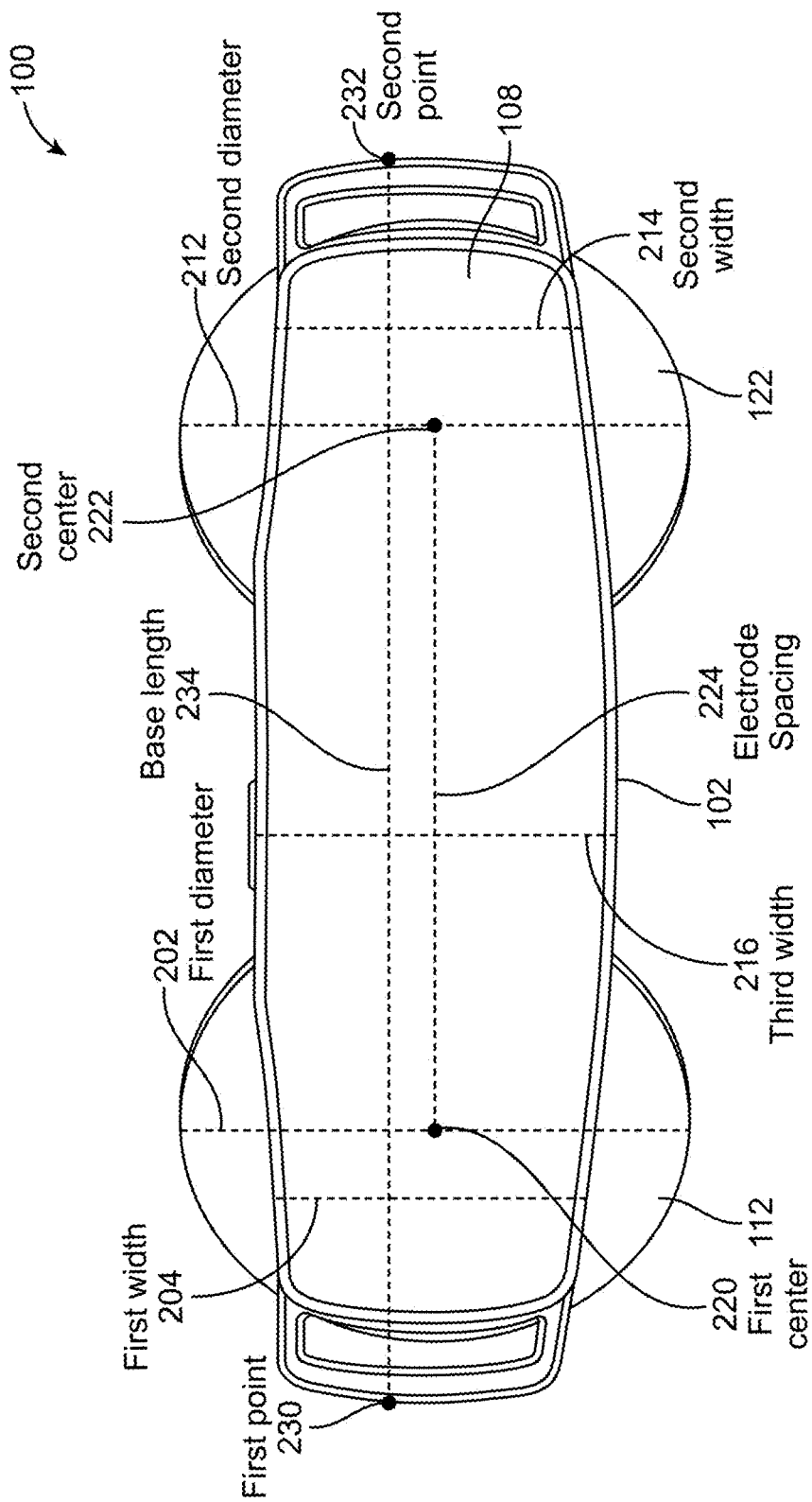
FIG. 2A illustrates a perspective view of an embodiment of a transcranial electrical stimulation device.
Figure 2C:
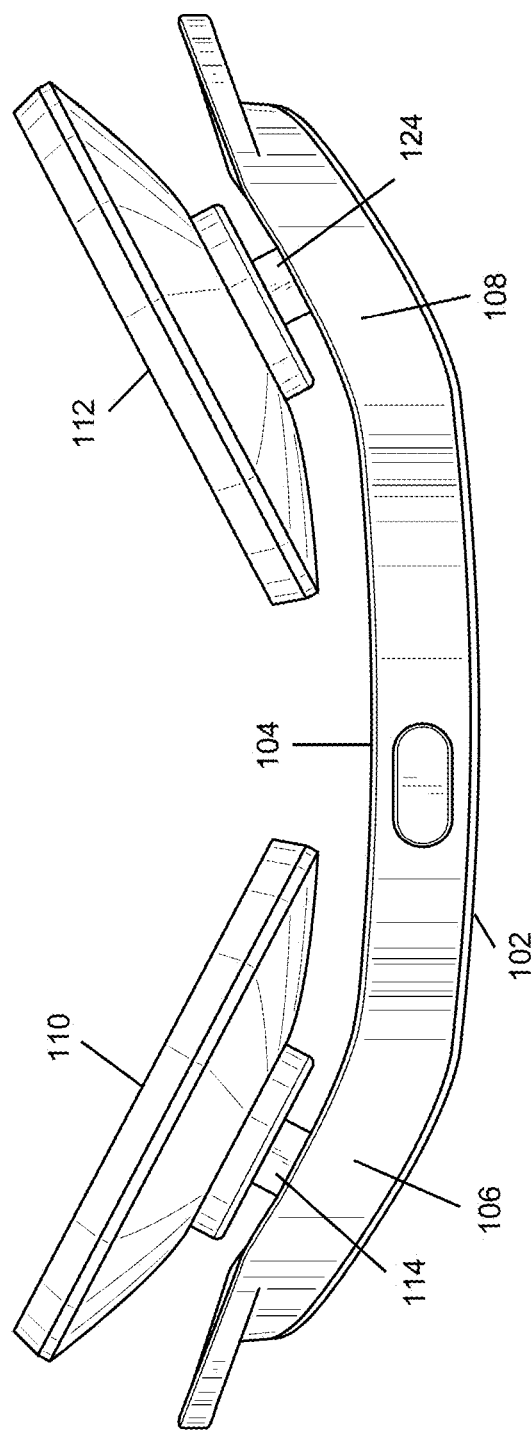
FIG. 2C is a front view of the transcranial electrical stimulation device shown in FIG. 2A.
Figure 2D:
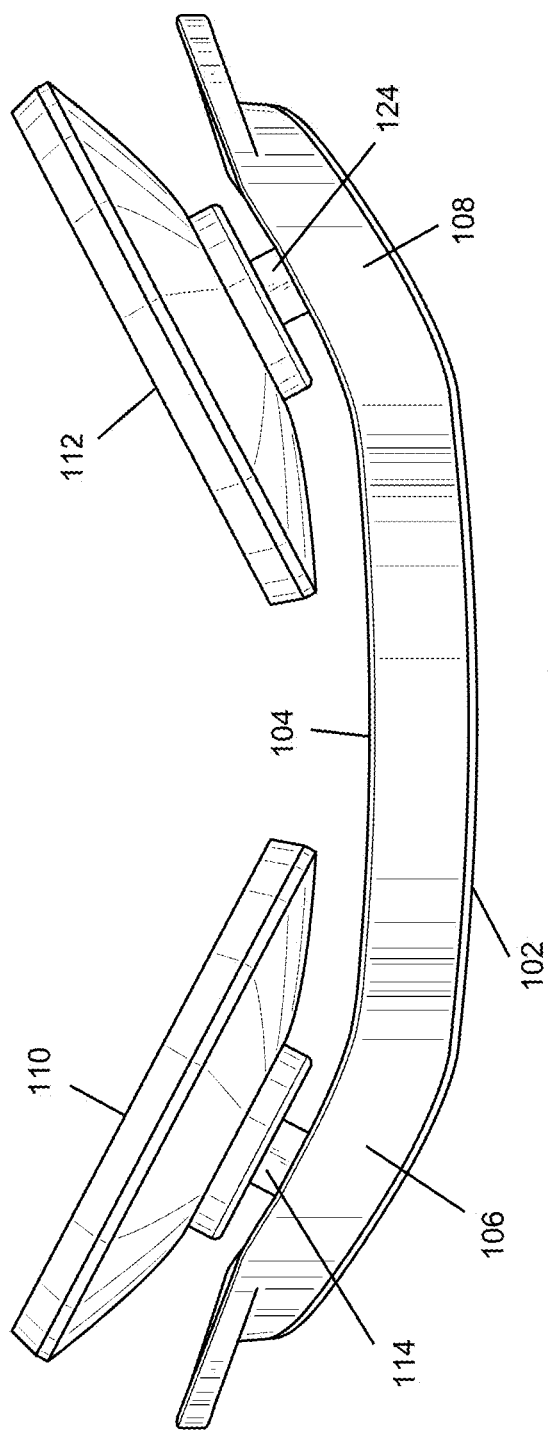
FIG. 2D is a rear view of the transcranial electrical stimulation device shown in FIG. 2A.
Figure 2E:
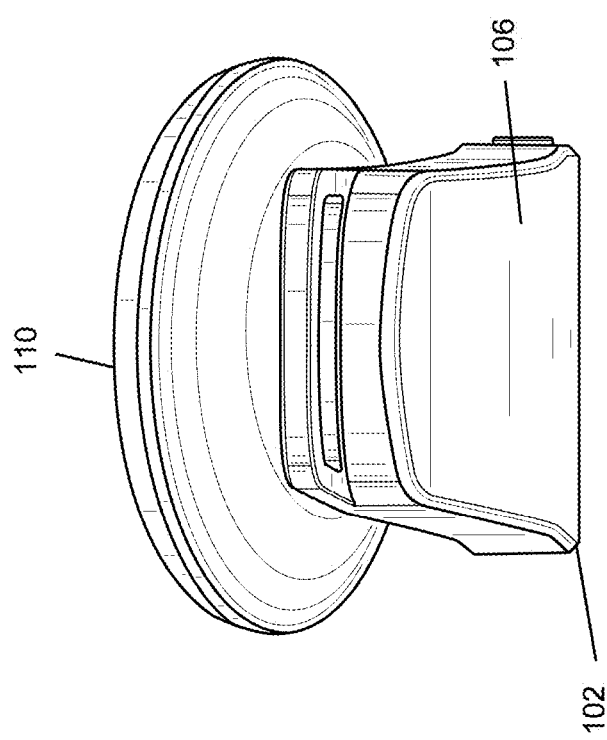
FIG. 2E is a left side view of the transcranial electrical stimulation device shown in FIG. 2A.
Figure 2G:
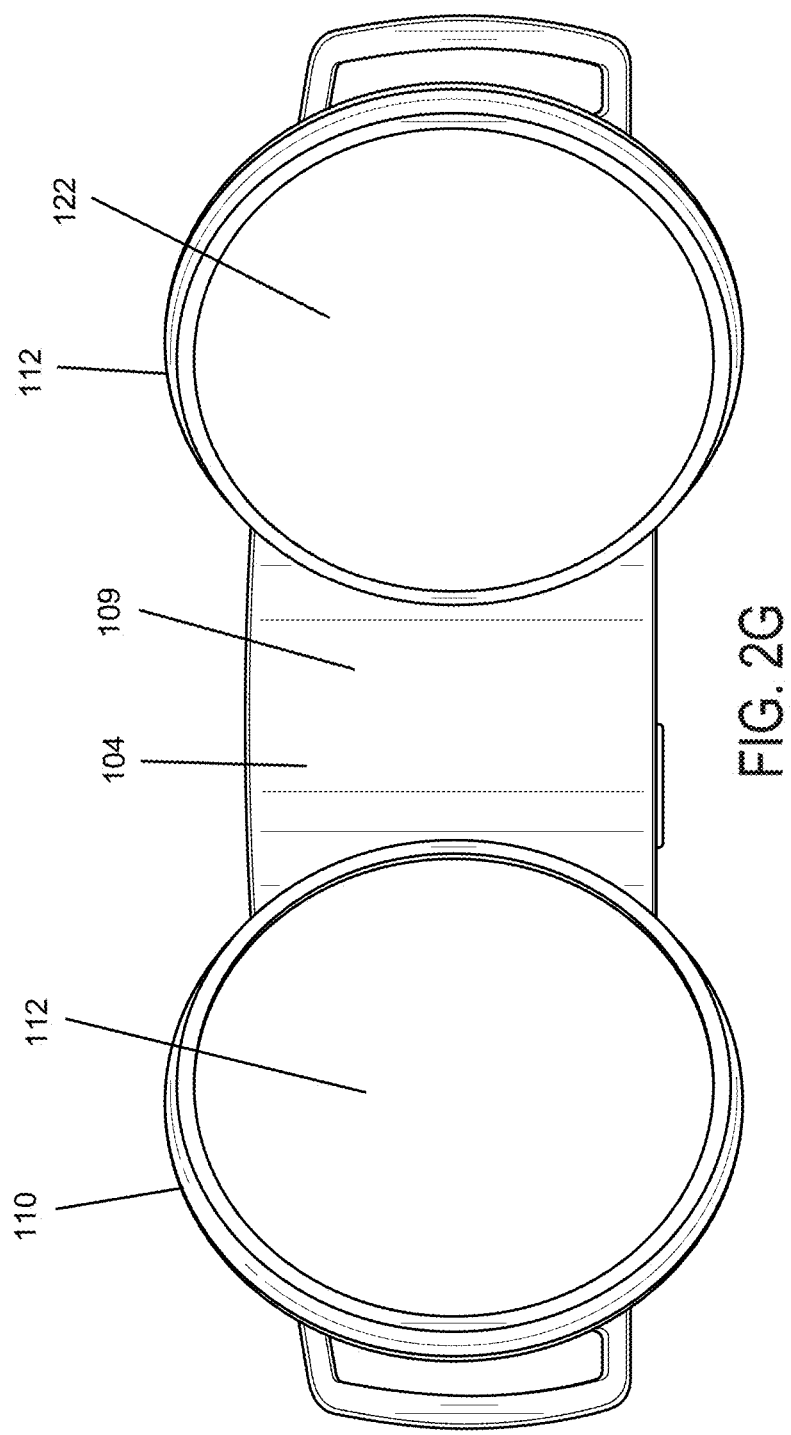
FIG. 2G is a bottom view of the transcranial electrical stimulation device shown in FIG. 2A.

The present solution provides devices, systems, and methods for improved transcranial electrical stimulation by using a compact and lightweight device that can allow a greater variety of users to more comfortably operate and wear the device for longer periods of time. In existing solutions, transcranial electrical stimulation devices may be bulky, non-portable, and difficult to operate, resulting in the overall lack of use and adoption of transcranial direct current stimulation as a technique to stimulate neuronal activity. The present solution can use a more ergonomic form factor having a size and weight low enough to be secured to the head of the user with a more comfortable securing device, such as a strap, and can use electrodes and components that couple the electrodes with a base of the device that have sufficient flexibility to conform to a variety of head shapes and sufficient resilience to maintain proper contact with users' heads during the course of stimulation. The present solution can enable the device to be operated in a first orientation (as shown in FIG. 2H) in which a first stimulation is performed, such as a first stimulation in which current flows from a first electrode into the head of the user, and into a second electrode, and a second orientation (as shown in FIG. 2I) (e.g., by flipping the device upside down or rotating the device 180 degrees about the axis extending through the end portions and the center portion) in which a second stimulation is performed in which the current can flow in an opposite direction through the head, enabling a greater variety of stimulation to be provided using the same device. In some embodiments, a transcranial electrical stimulation device includes a base. The base includes a center portion, a first end portion, a second end portion, and a first surface extending along the first end portion, the center portion, and the second end portion. The first end portion is connected to the center portion. The first end portion is angled relative to the center portion. The second end portion is opposite the first end portion and connected to the center portion. The second end portion is angled relative to the center portion. The first surface extends along the first end portion, the center portion, and the second end portion. The transcranial electrical stimulation device includes a first electrode attached to the first end portion and on the first surface. The first electrode includes a first conductive cup. The first electrode includes a first post attached to the first conductive cup and the first end portion. The first post includes a flexible material to allow the first conductive cup to bend about the first post. The transcranial electrical stimulation device includes a second electrode attached to the second end portion and on the first surface. The second electrode includes a second conductive cup. The second electrode includes a second post attached to the first conductive cup and the second end portion. The second post includes a flexible material to allow the second conductive cup to bend about the second post. The first electrode can be an anode and the second electrode can be a cathode. Electrical current can flow from the anode to the cathode.

A method for engaging in transcranial electrical stimulation can include securing a transcranial electrical stimulation device to a head of a user. The method can include initiating, by a control circuit, a stimulation session wherein the control circuit couples a power supply to a first electrode and a second electrode to enter a powered state. The method can include increasing, by the control circuit, a current to a first current level over a first period of time, wherein the current flows through the head of the user from a first electrode (i.e., anode) of the transcranial electrical stimulation device to a second electrode (i.e., cathode) of the transcranial electrical stimulation device. The method can include maintaining, by the control circuit, the current at the first current level over a second period of time. The method can include decreasing, by the control circuit, responsive to a termination condition, the current to second current level over a third period of time. The method can include terminating, by the control circuit, the stimulation session wherein the control circuit decouples the power supply to the first electrode and the second electrode to exit the powered state.

Figure 1:
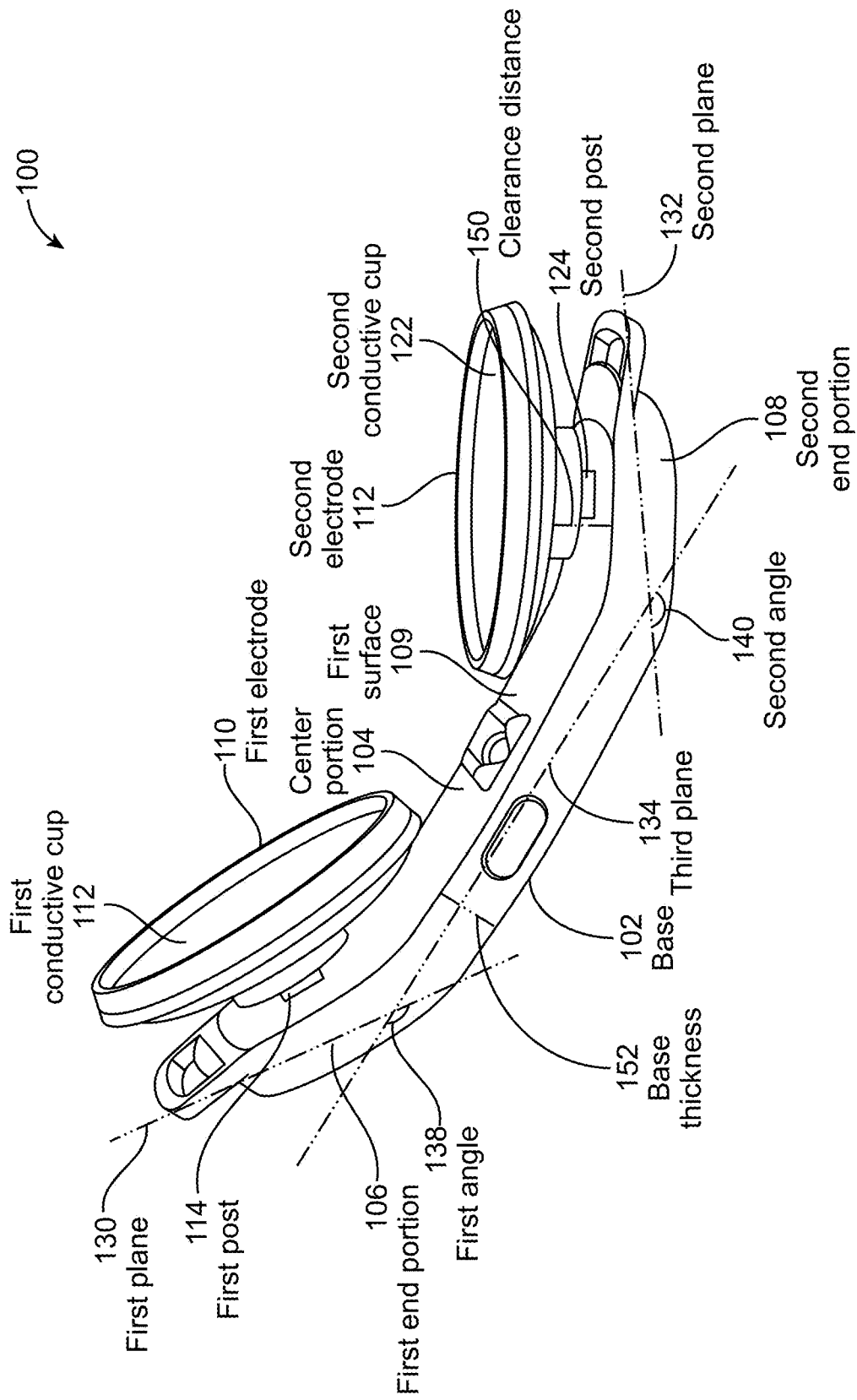
FIG. 1 illustrates a perspective view of an embodiment of a transcranial electrical stimulation device.

Referring to FIG. 1, a perspective view of an embodiment of a transcranial electrical stimulation device 100 is shown. The transcranial electrical stimulation device 100 can be a lightweight (e.g., less than 100 grams, less than 75 grams, or less than 50 grams) device adaptable to users with various head sizes. The transcranial electrical stimulation device 100 can include an external power supply and be portable. The transcranial electrical stimulation device 100 can have an operating temperature of 0° C. to 50° C. The transcranial electrical stimulation device 100 can be used for transcranial direct current stimulation (tDCS), transcranial alternating current stimulation (tACS), transcranial electrical stimulation (tES), transcranial random noise stimulation (tRNS), or cranial electrotherapy stimulation (CES), among others. The transcranial electrical stimulation device 100 can target the dorsolateral prefrontal cortex (DLPFC), the rostrolateral prefrontal cortex (RLPFC), the motor cortex or other regions of a user. DLPFC exists both on the right and the left side of the brain and is a subsection of the prefrontal cortex. DLPFC has been ascribed control or involvement in a variety of higher order cognitive functions such as cognition, attention, working memory, and decision-making as well as implicated in emotional, social, motivational and perceptual processes.

The transcranial electrical stimulation device 100 can include a base 102. The base 102 can be composed of plastic (e.g., polyethylene terephthalate, high-density polyethylene, polyvinyl chloride, low-density polyethylene, polypropylene, polystyrene, Styrofoam, polycarbonate, polyactide, acrylic, acrylonitrile butadiene, styrene, fiberglass, or nylon). The base 102 can include a center portion 104, a first end portion 106, and a second end portion 108. The base 102 can include a first surface 109 extending along the first end portion 106, the center portion 104, and the second end portion 108. The base 102 can include attachment points for the electrodes (described herein) and locations for various components (e.g., power button, light emitting diode, connection port described herein). The base 102 can be composed of an electrical insulator. The base 102 is or can include a housing to hold various components (e.g., internal circuitry, sensors, wires). The base 102 can have an exterior component that defines an interior of the base 102.

In some embodiments, the exposed surfaces of the center portion 104, the first end portion 106, and the second end portion 108 are free of any extensions or protrusions that restrict the device 100 from being worn by a user in a first orientation and a second orientation.

The center portion 104 can be connected to the first end portion 106 and the second end portion 108. The center portion 104 can include locations for various components (e.g., power button, light emitting diode, connection port described herein). The center portion 104 can be composed of plastic (e.g., polyethylene terephthalate, high-density polyethylene, polyvinyl chloride, low-density polyethylene, polypropylene, polystyrene, Styrofoam, polycarbonate, polyactide, acrylic, acrylonitrile butadiene, styrene, fiberglass, or nylon). The center portion 104 can define a third plane 134. The center portion 104 can be continuously connected to the first end portion 106. The center portion 104 can be continuously connected to the second end portion 108. The center portion 104 can surfaces center portion 104. For example, the center portion 104 can define a first surface 109. The center portion 104 can define a second surface 418 described herein. The first surface 109 can be substantially perpendicular to the second surface 418.

The first end portion 106 can be connected to the center portion 104. The first end portion 106 can be angled relative to the center portion 104. For example, a first plane 130 defined by the first end portion 106 can intersect the third plane 134 defined by the center portion 104 at a first angle 138. The first angle 138 can be greater than 90° (e.g., greater than 100°, greater than 135°, or greater than 160°). A first electrode 110 can be attached to the first end portion 106 and on the first surface 109. The first end portion 106 can be curved relative to the center portion 104. The curve can be parabolic.

The first electrode 110 can include a first conductive cup 112 and a first post 114. The first electrode 110 can be composed of a conductor (e.g., conductive silicone, conductive rubber). The first electrode 110 can be electrically connected to the second electrode 120 through the base 102. For example, the base 102 can include circuitry in the interior of the base 102 connecting the first electrode 110 to the second electrode 120.

The first conductive cup 112 can have a concave shape. The first conductive cup 112 can be composed of a conductor (e.g., conductive silicone, conductive rubber). The first conductive cup 112 can be composed of a conductive silicone compound elastomer. The first conductive cup 112 can be composed of conductive silicon with carbon. The first conductive cup 112 can be composed of a flexible material to bend and conform to the head of the user. The first conductive cup 112 can have a conductive area of 22.3 cm$^2$. The first conductive cup 112 can be connected to the first post 114. The first conductive cup 112 can be electrically connected to the first post 114. The first conductive cup 112 can include a non-conductive outer material (e.g., rubber, silicone).

The first post 114 can be attached to the first conductive cup 112 and the first end portion 106. The first post 114 can be composed of a flexible material to allow the first conductive cup 112 to bend about the first post 114. The first post 114 can have a rectangular prism shape. The first post 114 can have a cylindrical shape. The first post 114 can connect to the first conductive cup 112 through a locking mechanism (e.g., bar lock, pin lock, clip). The first post 114 can be molded into the first conductive cup 112. The first post 114 can be composed of a stiff material attached to a ball bearing. The first post 114 can pivot about the ball bearing.

The first post 114 can provide clearance for the first electrode 110 and the first surface 109. The first post 114 can space the first conductive cup 112 from the first surface 109 by a clearance distance 150. The clearance distance 150 can be greater than or equal to 0.25 centimeters and less than or equal to 2 centimeters. For example, the clearance distance 150 can be 0.5 centimeters. A ratio of the clearance distance to a thickness of the base is greater than or equal to 0.2 to 1 and less than or equal to 1.2 to 1. For example, the ratio of the clearance distance 150 to the thickness of the base can be 0.5 to 1. The thickness of the base member can be a base thickness 152.

The second end portion 108 can be connected to the center portion 104. The second end portion 108 can be angled relative to the center portion 104. For example, a second plane 132 defined by the second end portion 108 can intersect a third plane 134 defined by the center portion 104 at a second angle 140. The second angle 140 can be greater than 90° (e.g., 100°, 120°, 135°, 150°, 160°). A second electrode 120 can be attached to the second end portion 108 and on the first surface 109. The second end portion 108 can be curved relative to the center portion 104. The curve can be parabolic.

The second electrode 120 can include a second conductive cup 122 and a second post 124. The second electrode 120 can be composed of a conductor (e.g., conductive silicone, conductive rubber). The second electrode 120 can be electrically connected to the second electrode 120 through the base 102. For example, the base 120 can include circuitry in the interior of the base 102 connecting the second electrode 120 to the first electrode 110.

The second conductive cup 122 can have a concave shape. The second conductive cup 122 can be composed of a conductor (e.g., conductive silicone). The second conductive cup 122 can be composed of a conductive silicone compound elastomer. The second conductive cup 122 can be composed of conductive silicon with carbon. The second conductive cup 122 can be composed of a flexible material to bend and conform to the head of the user. The second conductive cup 122 can have a conductive area of 22.3 cm$^2$. The second conductive cup 122 can be connected to the second post 124. The second conductive cup 122 can be electrically connected to the second post 124. The second conductive cup 122 can include a non-conductive outer material (e.g., rubber, silicone).

The second post 124 can be attached to the second conductive cup 122 and the second end portion 108. The second post 124 can be composed of a flexible material to allow the second conductive cup 122 to bend about the second post 124. The second post 124 can have a rectangular prism shape. The second post 124 can have a cylindrical shape. The second post 124 can connect to the second conductive cup 122 through a locking mechanism (e.g., bar lock, pin lock, clip). The second post 124 can be molded into the second conductive cup 122. The second post 124 can be composed of a stiff material attached to a ball bearing. The second post 124 can pivot about the ball bearing. The second post 124 can provide clearance for the first electrode 110 and the first surface 109.

The second post 124 can provide clearance for the second electrode 112 and the first surface 109. The second post 124 can space the second conductive cup 122 from the first surface 109 by a clearance distance 150. The clearance distance 150 can be greater than or equal to 0.25 centimeters and less than or equal to 2 centimeters. For example, the clearance distance 150 can be 0.5 centimeters. A ratio of the clearance distance to a thickness of the base is greater than or equal to 0.2 to 1 and less than or equal to 1.2 to 1. For example, the ratio of the clearance distance 150 to the thickness of the base can be 0.5 to 1. The thickness of the base can be a base thickness 152.

As shown in FIG. 1, the first post and the corresponding first electrode and the second post and the corresponding second electrode extend outwardly from the first surface 109. The device is free of any components or extensions that extend outwardly from the first surface 109 or the center portion 104 of the device that would restrict a wearer of the device from wearing the device 100 in either a first orientation or a second orientation opposite the first orientation.

Referring to FIG. 2A-2I, FIG. 2A shows a perspective view of an embodiment of a transcranial electrical stimulation device 100. A first diameter 202 defined by the first conductive cup 112 can be greater than a first width 204 defined by the first end portion 106. The first diameter 202 can be between 4 cm and 7 cm, for example, 5.3 cm. The first width 204 can be between 2 and 4 cm, for example, 3 cm. A second diameter 212 defined by the second conductive cup 122 can be greater than a second width 214 defined by the second end portion 108. The second diameter 212 can be between 4 cm and 7 cm, for example, 5.3 cm. The second width 214 can be between 2 and 4 cm, for example, 3 cm. In some embodiments, the first diameter 202 defined by the first conductive cup 112 can be less than or equal to the first width 204 defined by the first end portion 106. The second diameter 212 defined by the second conductive cup 122 can be less than or equal to the second width 214 defined by the second end portion 108. A third width 216 defined by the center portion 104 can be between 3 cm and 5 cm, for example, 4 cm. The first diameter 202 and the second diameter 212 can be greater than the third width 216.

Figure 3:
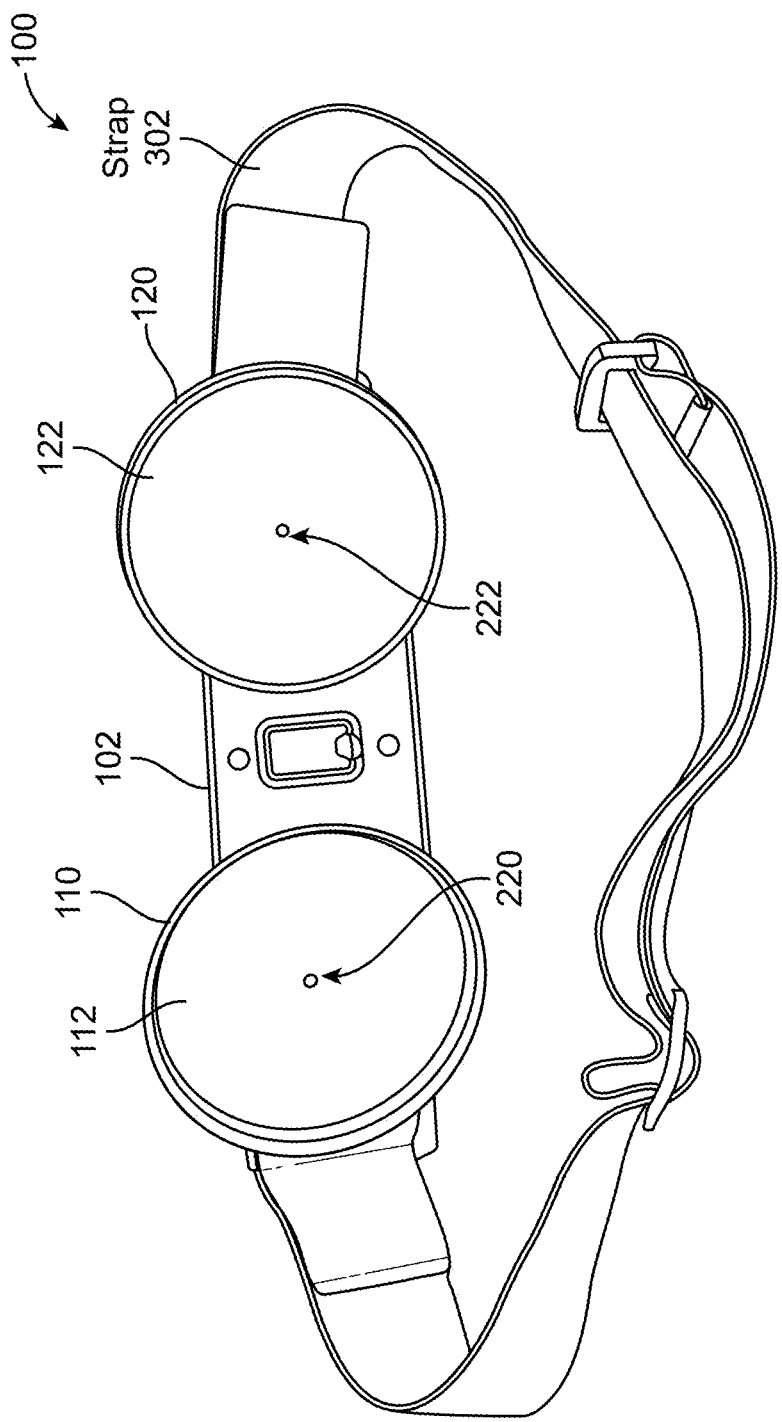
FIG. 3 illustrates a perspective view of an embodiment of a transcranial electrical stimulation device.

The first conductive cup 112 can define a first center 220 of the first conductive cup 112 (additionally depicted in FIG. 3). The second conductive cup 122 can define a second center 222 (additionally depicted in FIG. 3). The base 102 can include a first point 230 on the first end portion 106 and a second point 232 on the second end portion 108. The distance between the first point 230 on the first end portion 106 and the second point 232 on the second end portion 108 can define a base length 234. The base length 234 can be between 10 cm and 15 cm, for example, 13.6 cm. The distance between the first center 220 of the first conductive cup 112 and the second center 222 of the second conductive cup 122 can define an electrode spacing 224. The electrode spacing 224 can be between 5 cm and 10 cm, for example, 7 cm. The base length 234 can be greater than or equal to the electrode spacing 224.

Referring to FIG. 3, a perspective view of an embodiment of a transcranial electrical stimulation device 100 is shown. The transcranial electrical stimulation device 100 can include a strap 302. The strap 302 can be attached to the base 102 at the first end portion 106 and at the second end portion 108. The strap 302 can be composed of elastic materials (e.g., rubber, elastic fibers, spandex, elastane, polyester, cotton). The strap 302 can include hook-and-loop fasteners to attach the strap 302 to the first end portion 106 and to the second end portion 108. The strap 302 can extend from the first end portion 106 to the second end portion 108. The strap 302 can be configured to secure the first electrode 110 and the second electrode 120 to a head of a user. The strap 302 can be adjustable. The strap can be adjusted on the head of the user to allow the first electrode 110 and the second electrode 120 to contact the head of the user. The first conductive cup 112 and the second conductive cup 122 can contour to the head of the user. Contouring to the head of the user can include the surfaces of the first conductive cup 112 and the surfaces of the second conductive cup 122 lying flush against the head of the user. The first center 220 of the first conductive cup 112 and the second center 222 of the second conductive cup 122 is shown. The first conductive cup 112 can define a first center 220 of the first conductive cup 112. The second conductive cup 122 can define a second center 222.

In some embodiments, the strap 302 can include a retaining device. The retaining device can wrap partially or entirely around the head of a user. The retaining device can be composed of plastic. The strap 302 can include a headband. The strap 302 can be composed of synthetic fibers (e.g., nylon, spun polyester, textured polyester, polypropylene, among others). The strap 302 can be composed of natural materials (e.g. hemp, leather, cotton, jute, among others). The strap 302 can include a retaining device that fits most or all head sizes.

Figure 4:
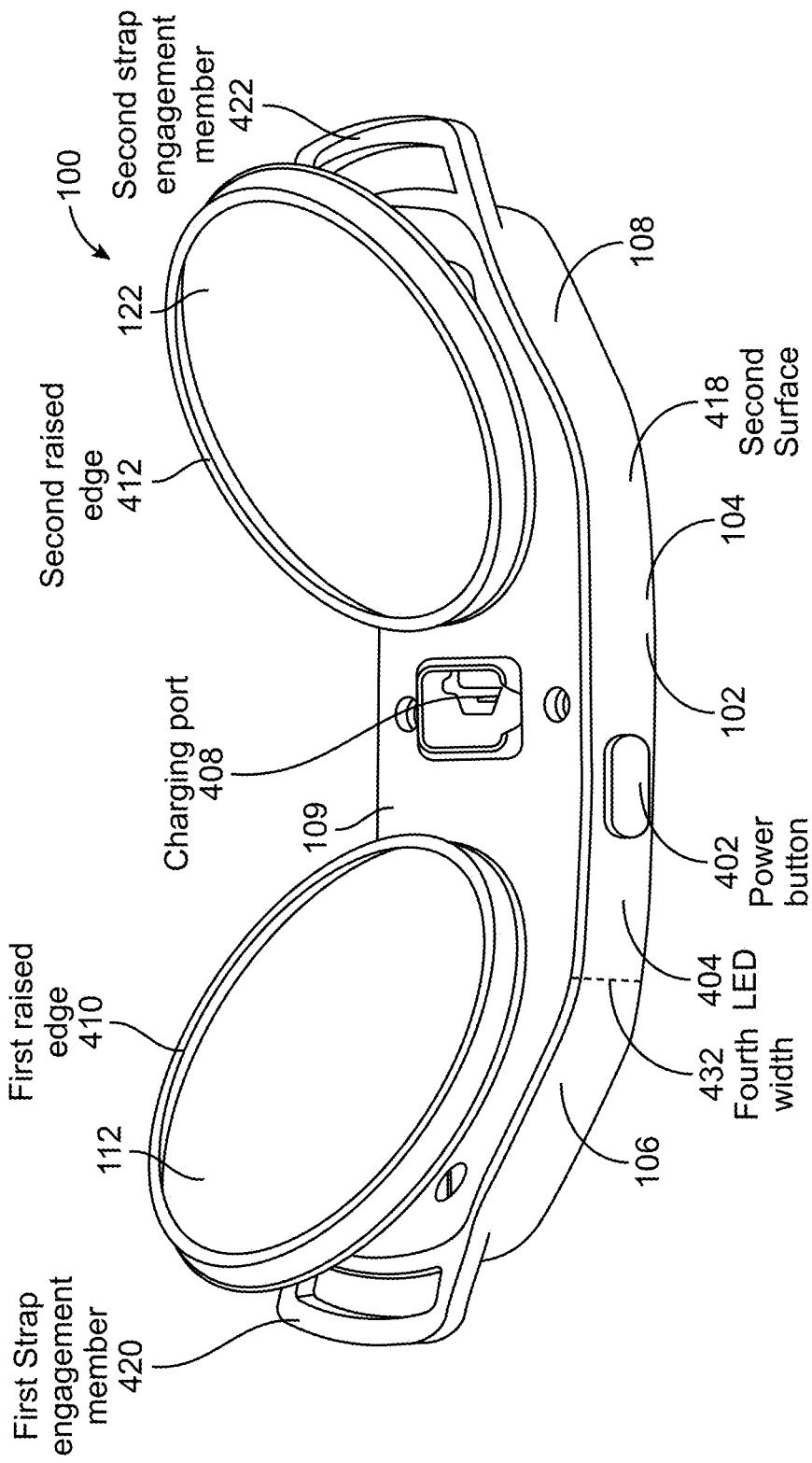
FIG. 4 illustrates a perspective view of an embodiment of a transcranial electrical stimulation device.

Referring to FIG. 4, a perspective view of an embodiment of a transcranial electrical stimulation device 100 is shown. The transcranial electrical stimulation device 100 can include a charging port 408 disposed on the first surface 109 of the base 102. The charging port 408 can be disposed on the center portion 104 of the base 102. The charging port 408 can be a universal serial bus (USB) port (e.g., USB-B, USB-A, micro USB, mini USB, USB Type C, among others). A cover 540 (described herein) can be removably attached to the charging port 408 to provide protection to the charging port 408 when the transcranial electrical stimulation device 100 is not charging. A fourth width 432 defined by the center portion 104 can be between 1 cm and 2 cm, for example, 1.1 cm.

The charging port 408 of the transcranial electrical stimulation device 100 can be configured to also be a communication port through which data from the device 100 can be communicated with one or more other computing devices, such as a mobile phone, a smartphone, a tablet, or other computing device. In some embodiments, the transcranial electrical stimulation device 100 can include a separate communication port through which data from the device 100 can be communicated with one or more other computing devices. In some embodiments, the communication port can be a wireless communication port, such as a port that can communicate with other computing devices via BLUETOOTH, Wi-Fi, cellular, or any other wireless connection.

The transcranial electrical stimulation device 100 can be configured to include a processor and memory for storing data. The data can include user profile information of a user of the device 100, for instance, data corresponding to certain settings according to which to conduct the stimulation session. The data can also include any information corresponding to when a session was initiated, terminated, or interrupted, among others. The information can be stored in the memory of the device 100. The information can then be transmitted to one or more computing devices via the communication port of the device 100.

In some embodiments, the device can be configured to allow a user to select a particular stimulation session type from a plurality of different stimulation session types. The different stimulation session types can be preset and prestored in the memory of the device. The different session types can include different stimulation parameters, including different lengths of time of the session, different amplitudes of the current including one or more current amplitude patterns over the duration of the session, among others. The current amplitude patterns can include a ramp up pattern, a ramp down pattern and any other patterns during the course of the stimulation session. The device can include a button or other input selection component that allows the user to select from a particular stimulation session type from the plurality of different stimulation session types. In some embodiments, the amplitude of the current can be 0.1 mA, 0.5 mA, 1 mA, 1.1 mA, 1.2 mA, 1.3 mA, 1.4 mA, 1.5 mA, 1.6 mA, 1.7 mA, 1.8 mA, 1.9 mA, 2 mA, 2.1 mA, 2.2 mA, 2.3 mA, 2.4 mA, 2.5 mA, 2.6 mA, 2.7 mA, 2.8 mA, 2.9 mA, 3 mA, 3.1 mA, 3.2 mA, 3.3 mA, 3.4 mA, 3.5 mA, 3.6 mA, 3.7 mA, 3.8 mA, 3.9 mA, 4 mA, or 5 mA. In some embodiments, the length of the session can vary between 5 minutes to 60 minutes. In particular, the length of the session can be 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, or 60 minutes.

As described herein, the device is configured to be operated in two orientations. In some embodiments, the plurality of different stimulation session types a user can select from can vary based on the orientation in which the device is worn by the user. For instance, if the device is worn in the first orientation (as shown in FIG. 2H), stimulation session types 1, 2 and 3 may be available for selection. If the device is worn in the second orientation (as shown in FIG. 2I), stimulation session types 1, 4 and 5 may be available for selection. The device can include one or more sensors that allow the processor to determine the orientation in which the device is worn and therefore, can be able to determine which stimulation session type to provide to the electrodes based on the orientation in which the device is worn.

The transcranial electrical stimulation device 100 can include a second surface 418. The second surface 418 can extend along the first end portion 106, the center portion 102 and the second end portion 108. The transcranial electrical stimulation device 100 can include a power button 402. The power button 402 can be disposed on the second surface 418. The power button 402 can be disposed on the center portion 102 of the base 102. In some embodiments, the button can be positioned anywhere on the device including the first end portion 106 or the second end portion 108.

The transcranial electrical stimulation device 100 can include a light emitting diode ("LED") 404. The LED 404 can be disposed on the second surface 418. The LED 404 can be disposed on the center portion 102 of the base 102. The electrical connections of the LED 404 can be housed in the interior of the base 102. The LED 404 can emit light of various colors, such as red, green and blue. The LED 404 can emit light to indicate a status of the transcranial electrical stimulation device 100. The LED 404 can indicate battery supply or battery capacity of the transcranial electrical stimulation device 100.

The transcranial electrical stimulation device 100 can include a first strap engagement 420. The first strap engagement 420 can be disposed on the first end portion 106. The first strap engagement 420 can provide a geometry to removably attach the strap 302 to the transcranial electrical stimulation device 100. The first strap engagement 420 can define a deadeye geometry for the strap 302 to attach to the first strap engagement 420. The first strap engagement 420 can be a handle for the strap 302 to attach to the first strap engagement 420. The first strap engagement 420 can contact a hook-and-loop fastener of the strap 302.

The transcranial electrical stimulation device 100 can include a second strap engagement 422. The second strap engagement 422 can be disposed on the second end portion 108. The second strap engagement 422 can provide a geometry to removably attach the strap 302 to the transcranial electrical stimulation device 100. The second strap engagement 422 can define a deadeye geometry for the strap 302 to attach to the first strap engagement 420. The second strap engagement 422 can be a handle for the strap 302 to attach to the second strap engagement 422. The second strap engagement 422 can contact a hook-and-loop fastener of the strap 302.

The first conductive cup 112 of the transcranial electrical stimulation device 100 can include a first raised edge 410. The first raised edge 410 can provide a shallow wall for the concave shape of the first conductive cup 112. The second conductive cup 122 of the transcranial electrical stimulation device 100 can include a second raised edge 412. The second raised edge 412 can provide a shallow wall for the concave shape of the second conductive cup 122. The first conductive cup 112 can hold a sponge 900 to directly contact the head of a user. The first conductive cup 112 can securely hold the sponge 900 to the head of the user. The second conductive cup 122 can hold a sponge 900 to directly contact the head of the user. The second conductive cup 122 can securely hold the sponge 900 to the head of the user.

Figure 5:
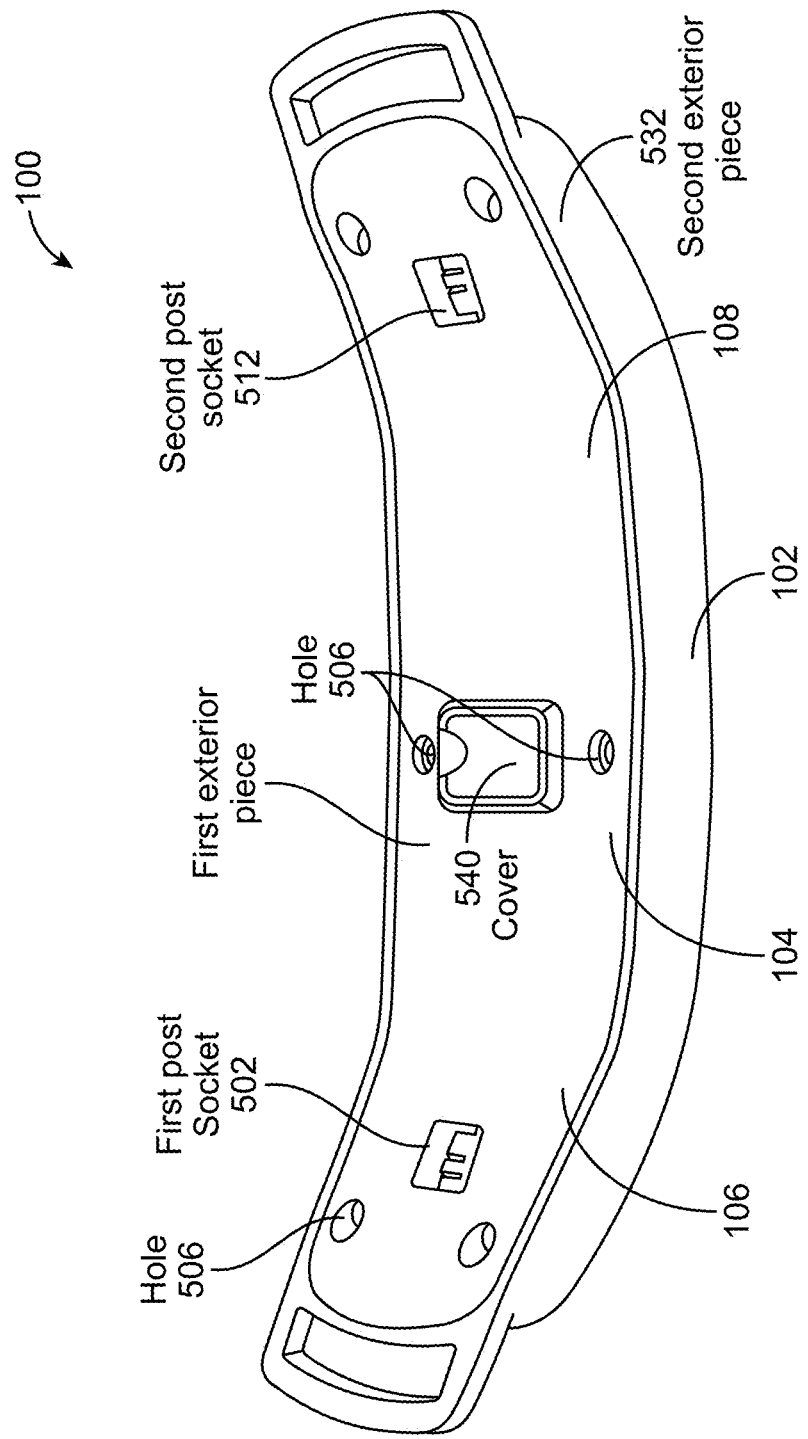
FIG. 5 illustrates a perspective view of an embodiment of a transcranial electrical stimulation device without electrodes.

Referring to FIG. 5, a perspective view of an embodiment of a transcranial electrical stimulation device 100 without electrodes is shown. The transcranial electrical stimulation device 100 is shown without the first electrode 110 and the second electrode 120. The base 102 can include a first post socket 502, a second post socket 512 and one or more holes 506.

The transcranial electrical stimulation device 100 can include the first post socket 502. The first post 114 can insert into the first post socket 502. The first post socket 502 can receive the first post 114. The first post socket 502 can include an attachment mechanism or locking mechanism (e.g., bar lock, pin lock 614 as described with reference to FIG. 6, clip). The first electrode 110 can be removably attached to the first end portion 106. The first post 114 of the first electrode 110 can be removably attached to the first post socket 502 of the first end portion 106.

The transcranial electrical stimulation device 100 can include the second post socket 512. The second post 124 can insert into the second post socket 512. The second post socket 512 can receive the second post 124. The second post socket 512 can include an attachment mechanism or locking mechanism (e.g., bar lock, pin lock, clip). The second electrode 120 can be removably attached to the second end portion 108. The second post 124 of the second electrode 120 can be removably attached to the second post socket 512 of the second end portion 108.

The transcranial electrical stimulation device 100 can include one or more holes 506. The one or more holes 506 can be disposed on the center portion 104, first end portion 106, or the second end portion 108. The one or more holes 506 can be disposed on the first surface 109. The one or more holes 506 can be threaded holes to allow a locking mechanism (e.g., screw) to hold a first exterior piece 530 to the second exterior piece 532. The first surface 109 can define the first exterior piece 530. The second surface 418 can define the second exterior piece 532.

The charging port 408 of the transcranial electrical stimulation device 100 can include a cover 540. The cover 540 can protect the charging port 408 from damage. The cover 540 can be attached to the base 102 of the transcranial electrical stimulation device 100. The cover 540 can lay on top of the charging port 408. The cover 540 can be removably attached to the base 102.

Figure 6:
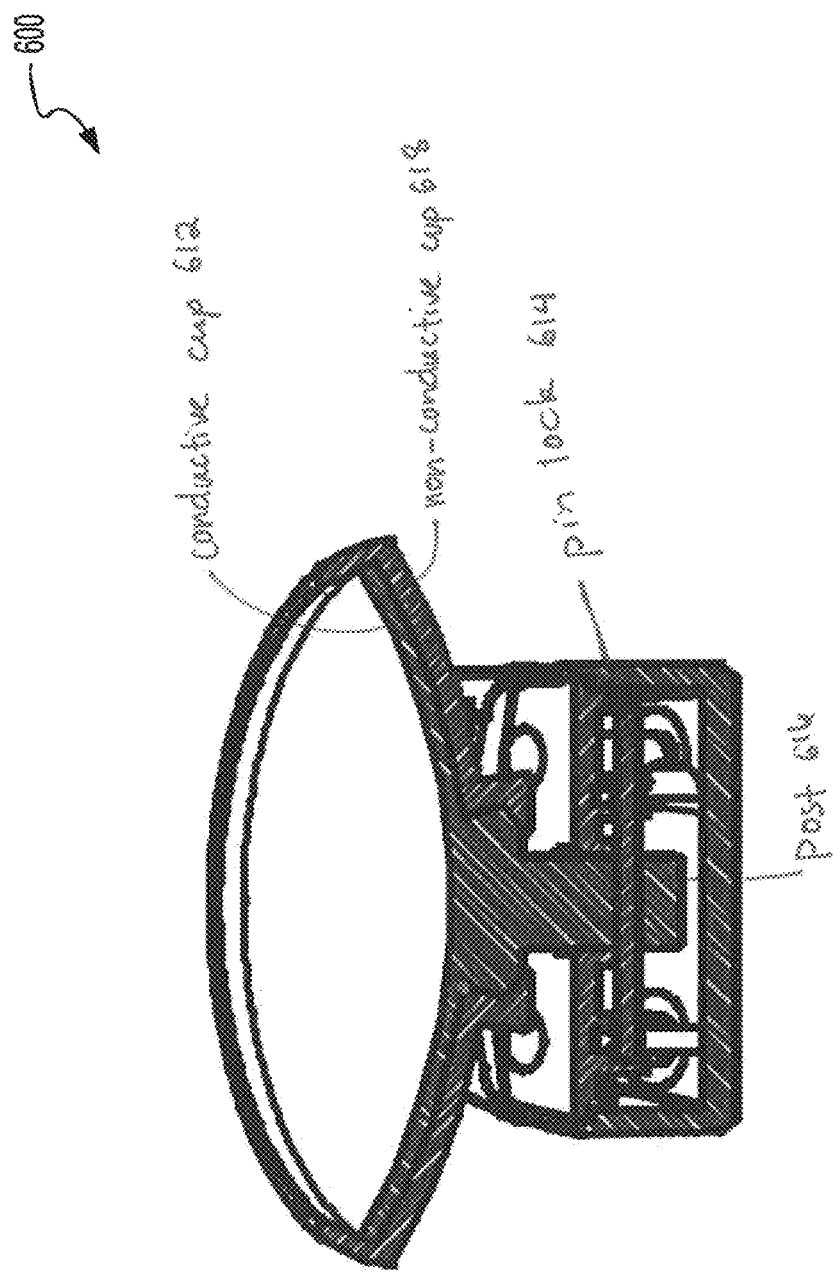
FIG. 6 illustrates a perspective view of an embodiment of an electrode of a transcranial electrical stimulation device.

Referring to FIG. 6, a perspective view of an embodiment of an electrode 600 of a transcranial electrical stimulation device 100. The electrode 600 can include the first electrode 110 or the second electrode 120. The electrode 600 can include a conductive cup 612. The conductive cup can include the first conductive cup 112 or the second conductive cup 122. The electrode 600 can include a pin lock 614 to secure the post 616 to a back-side cover 830. The post 616 can be a conductive portion. The back-side cover 830 can be a non-conductive portion. The pin lock 614 can be composed of a conductive material. The electrode 600 can include a non-conductive cup 618. The non-conductive cup can include a first non-conductive cup 812 or a second non-conductive cup 822. Current can be provided via the pin lock 614 to the post 616. Current can be provided via the post 616 to the conductive cup 612. The pin lock 614 can secure the first conductive cup 112 to the base 102. The pin lock 614 can secure the second conductive cup 122 to the base 102.

Figure 7:
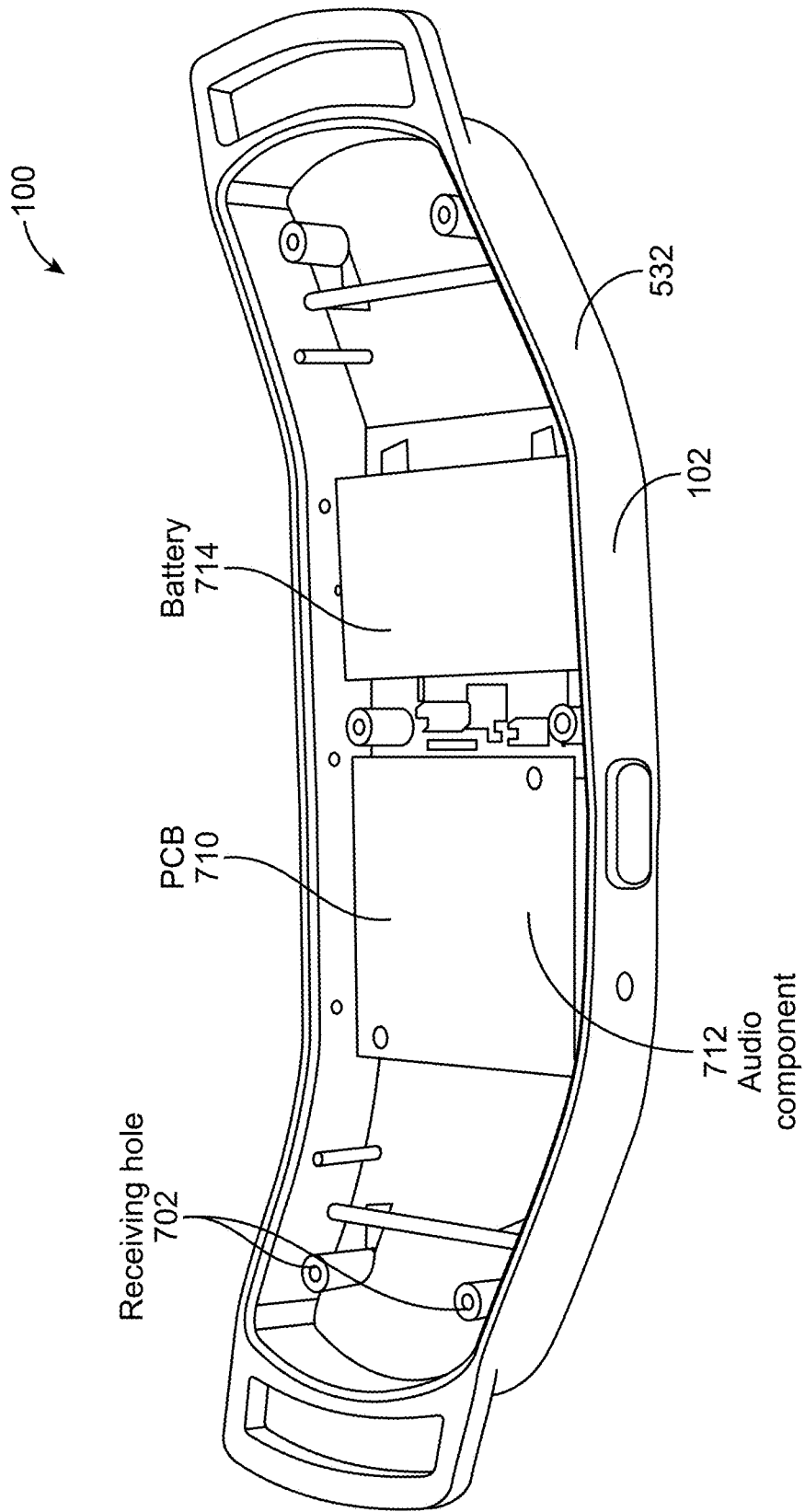
FIG. 7 illustrates a perspective view of an embodiment of a transcranial electrical stimulation device interior.

Referring to FIG. 7, a perspective view of an embodiment of a transcranial electrical stimulation device 100 interior is shown. The transcranial electrical stimulation device 100 is shown without the first exterior piece 530. The second exterior piece 532 of the base 102 is shown. The second exterior piece 532 includes one or more receiving holes 702. The one or more receiving holes 702 can receive a locking mechanism (e.g., screw) to secure the first exterior piece 530 to the second exterior piece 532. The one or more holes 702 can be threaded holes. The one or more holes 702 can be disposed on the surface of the second exterior piece 532. The one or more holes 702 can be disposed on the interior surface of the base 102.

The transcranial electrical stimulation device 100 can include a printed circuit board (PCB) 710. The PCB 710 can include wired connections to the charging port 408, the LED 404 and the power button 402. The PCB 710 can include wired connections to the first electrode 110 and to the second electrode 112. The PCB 710 can include wired connections to the pin lock 614. The PCB 710 can include a control circuit 802 described in detail herein. The PCB 710 can include wired connections to an audio component 712 and a battery 714.

The audio component 712 can include a component of the transcranial electrical stimulation device 100 that makes sounds to signal an operation state of the transcranial electrical stimulation device 100. The audio component can include a piezoelectric buzzer. The audio component 712 can be controlled by a control circuit to signal different operational states or modes of the transcranial electrical stimulation device 100. For example, an operational state or mode can include a properly secured transcranial electrical stimulation device 100. An operation state or mode can include an increasing current of the transcranial electrical stimulation device 100. An operation state or mode can include a decreasing current. An operation state or mode can include a transcranial electrical stimulation device 100 that has been removed from the head of the user by accident. An operation state or mode can include the termination of the stimulation session. An operation state or mode can include ending the stimulation session early.

The battery 714 can power the transcranial electrical stimulation device 100 during the stimulation sessions. For example, the battery 714 can be charged by connecting a charging cable to the charging port 408. The battery 714 can take four hours to fully charge. The battery can provide for more than 30 stimulation sessions when fully charged. The battery 714 can be incapable of being changed when the transcranial electrical stimulation device 100 is in a powered state. The battery 714 can include an external power supply. The battery 714 can include a lithium-ion battery. The battery can operate at 3.7V and 250 mAh.

The transcranial electrical stimulation device 100 can include a sensor to detect orientation of the transcranial electrical stimulation device 100. For example, the transcranial electrical stimulation device 100 can include an accelerometer. The transcranial electrical stimulation device 100 can include a tilt sensor to measure the tilt of the transcranial electrical stimulation device 100 with reference to gravity. The transcranial electrical stimulation device 100 can change the direction of the flow of current based on the orientation of the transcranial electrical stimulation device 100. The direction of the flow of current can be controlled by user input.

Figure 8:
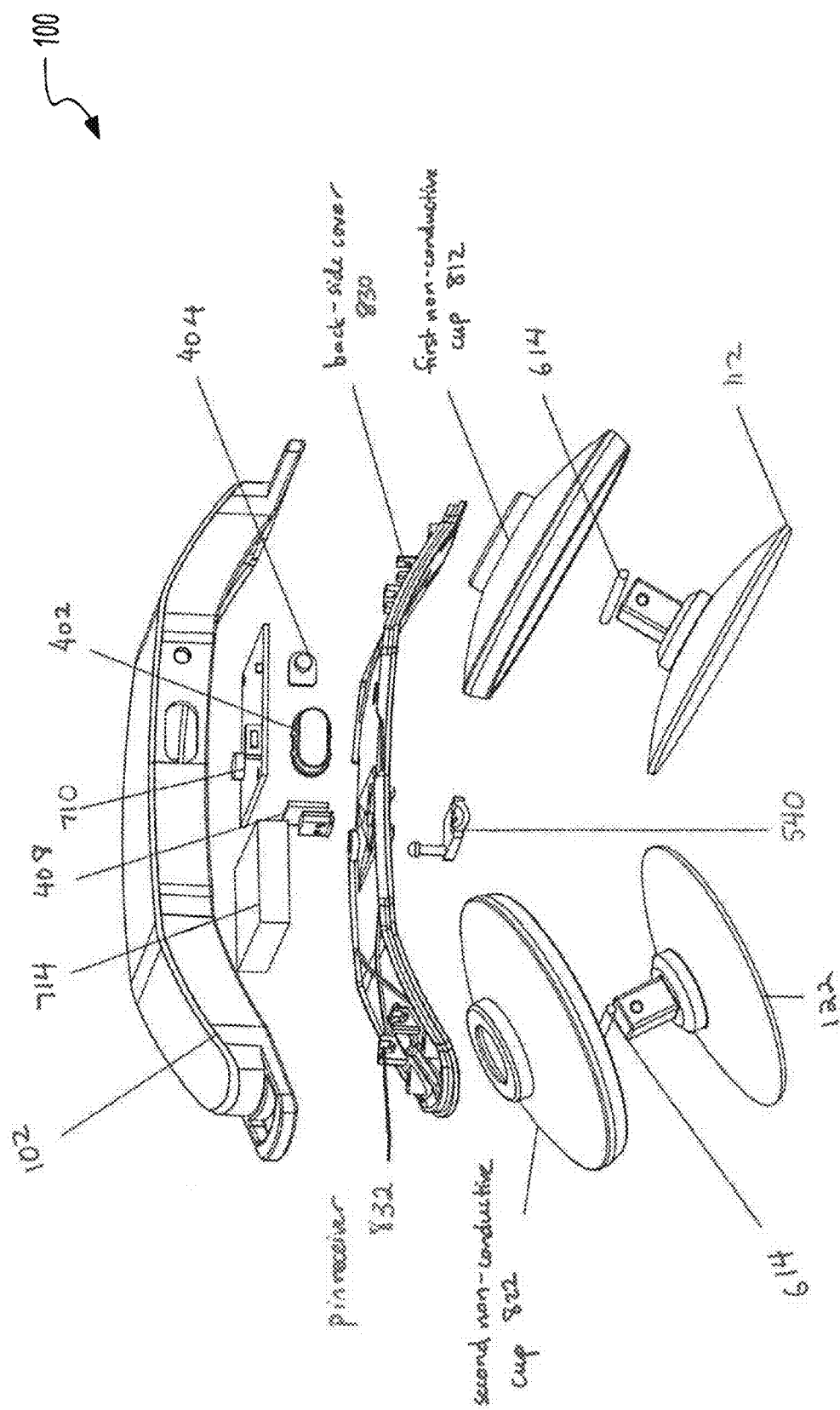
FIG. 8 illustrates an exploded view of an embodiment of a transcranial electrical stimulation device.

Referring to FIG. 8, an exploded view of an embodiment of a transcranial electrical stimulation device 100. The transcranial electrical stimulation device 100 can include a first non-conductive cup 812 (e.g., non-conductive portion of first conductive cup 112) and a second non-conductive cup 822 (e.g., non-conductive portion of second conductive cup 122). The first non-conductive cup 812 can be composed of an insulator (e.g., silicone, rubber). The first conductive cup 112 can nestle into the first non-conductive cup 812. The first conductive cup 112 can be joined to the first non-conductive cup 812 by molding, an adhesive (e.g., gluing), or via operation of a pin lock 614. The first conductive cup 112 can have a diameter of 5.3 cm. The first non-conductive cup 812 can have a diameter of 5.3 cm. The second non-conductive cup 822 can be composed of an insulator (e.g., silicone, rubber). The second conductive cup 122 can nestle into the second non-conductive cup 822. The second conductive cup 122 can be joined to the second non-conductive cup 822 by molding, an adhesive (e.g., gluing), or via operation of a pin lock 614. The second conductive cup 122 can have a diameter of 5.3 cm. The second non-conductive cup 822 can have a diameter of 5.3 cm. The transcranial electrical stimulation device 100 can include a back-side cover 830. The back-side cover 830 can include a pin receiver 832. The pin receiver 832 can receive a pin lock 614. The pin receiver 832 can have a notch to lock the electrode 600 to the back-side cover 830.

Figure 9:
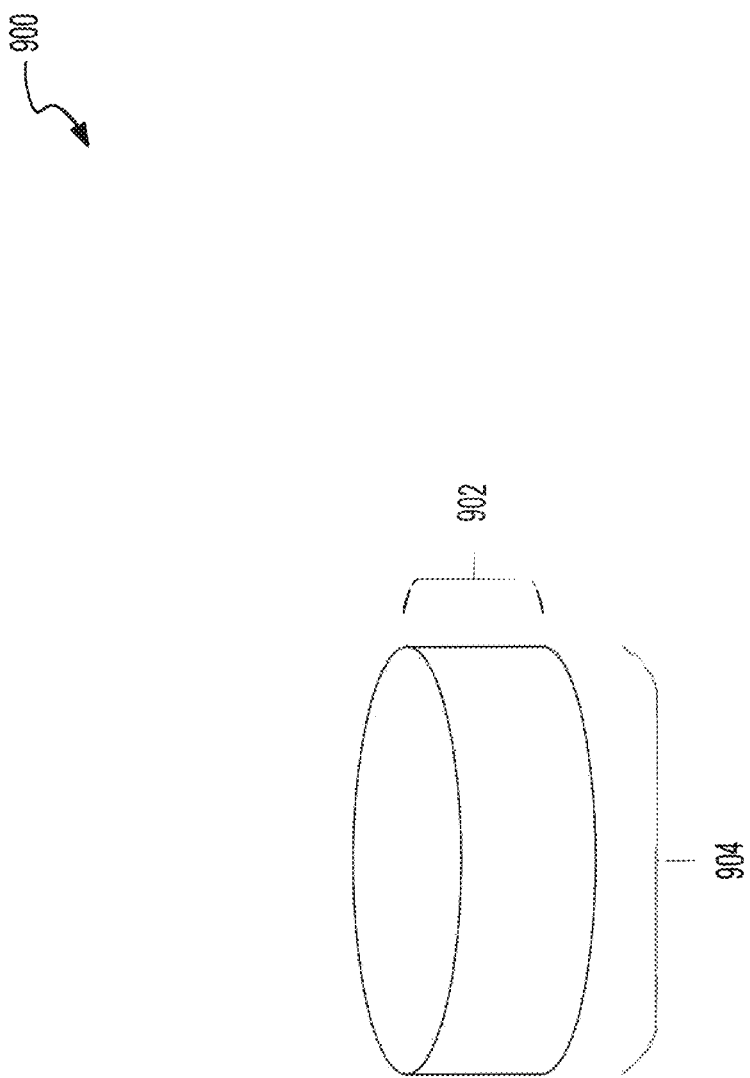
FIG. 9 illustrates a block diagram of an embodiment of a sponge.

Referring to FIG. 9, a block diagram representation of one embodiment of a sponge 900 is shown. A sponge height 902 defined by the sponge 900 can be greater than a thickness defined by the first raised edge 410. The sponge height 902 can be greater than a thickness defined by the second raised edge 412. A sponge width 904 defined by the sponge 900 can be less than the first diameter 202. The sponge width 904 can be less than the second diameter 212. The sponge 902 can fit securely into the first conductive cup 112. The sponge 902 can fit securely into the second conductive cup 122. The sponge 900 can be pre-soaked in a saline solution before operation of the transcranial electrical stimulation device 100. The sponge 900 can include various shapes (e.g., rectangular prism, cube, elliptic cylinder, among others). The sponge 900 can expand when soaked in saline solution.

Figure 10:
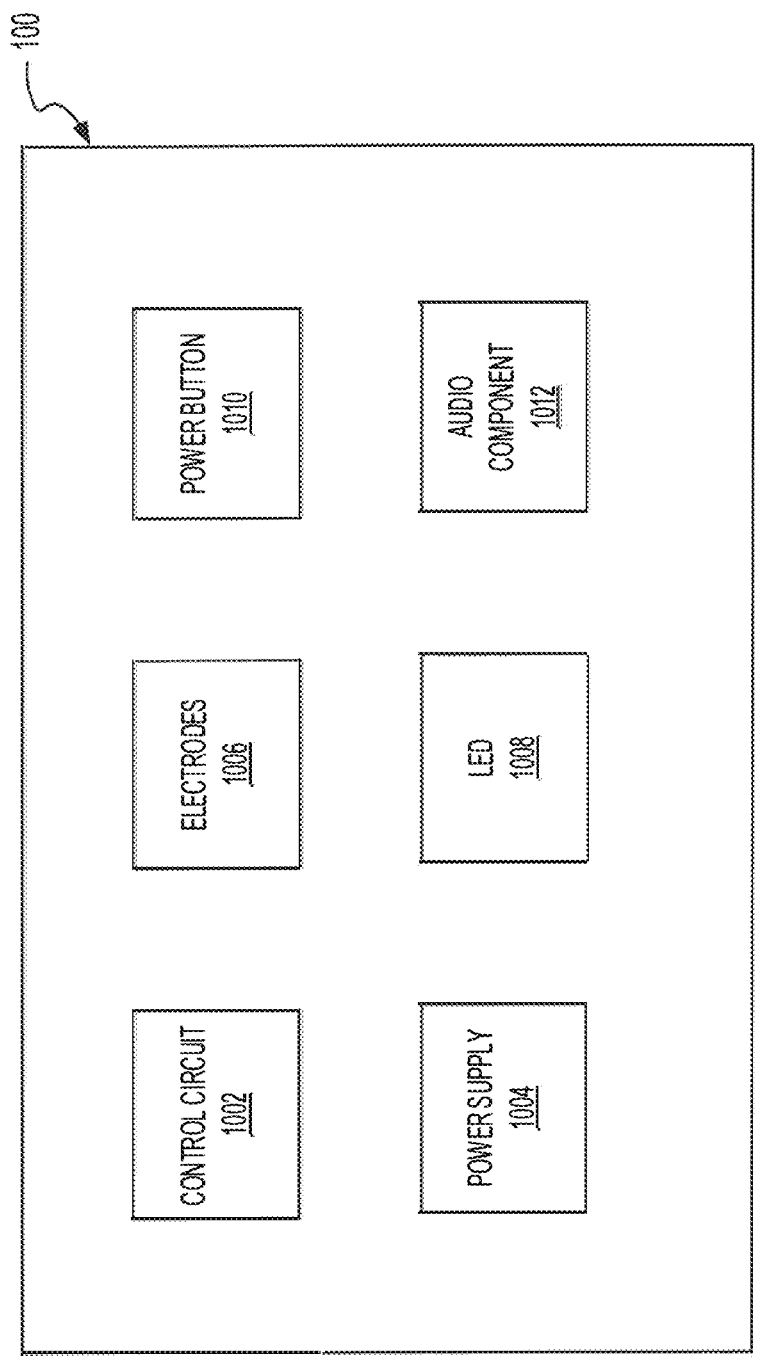
FIG. 10 illustrates a block diagram of an embodiment of a transcranial electrical stimulation device.

Referring to FIG. 10, a block diagram representation of one embodiment of device components is shown. The transcranial electrical stimulation device 100 can include a control circuit 1002, a power supply 1004, electrodes 1006, a LED 404, a power button 1010 and an audio component 712. The power supply 1004 can include the battery 714 described in a previous section of the disclosure. Electrodes 1006 can include the first electrode 110 and the second electrode 112. The LED 1008 can include the LED 404 described in a previous section of the disclosure. The power button 1010 can include the power button 402 described in a previous section of the disclosure. The audio component 1012 can include the audio component 712 described in a previous section of the disclosure.

Figure 11:
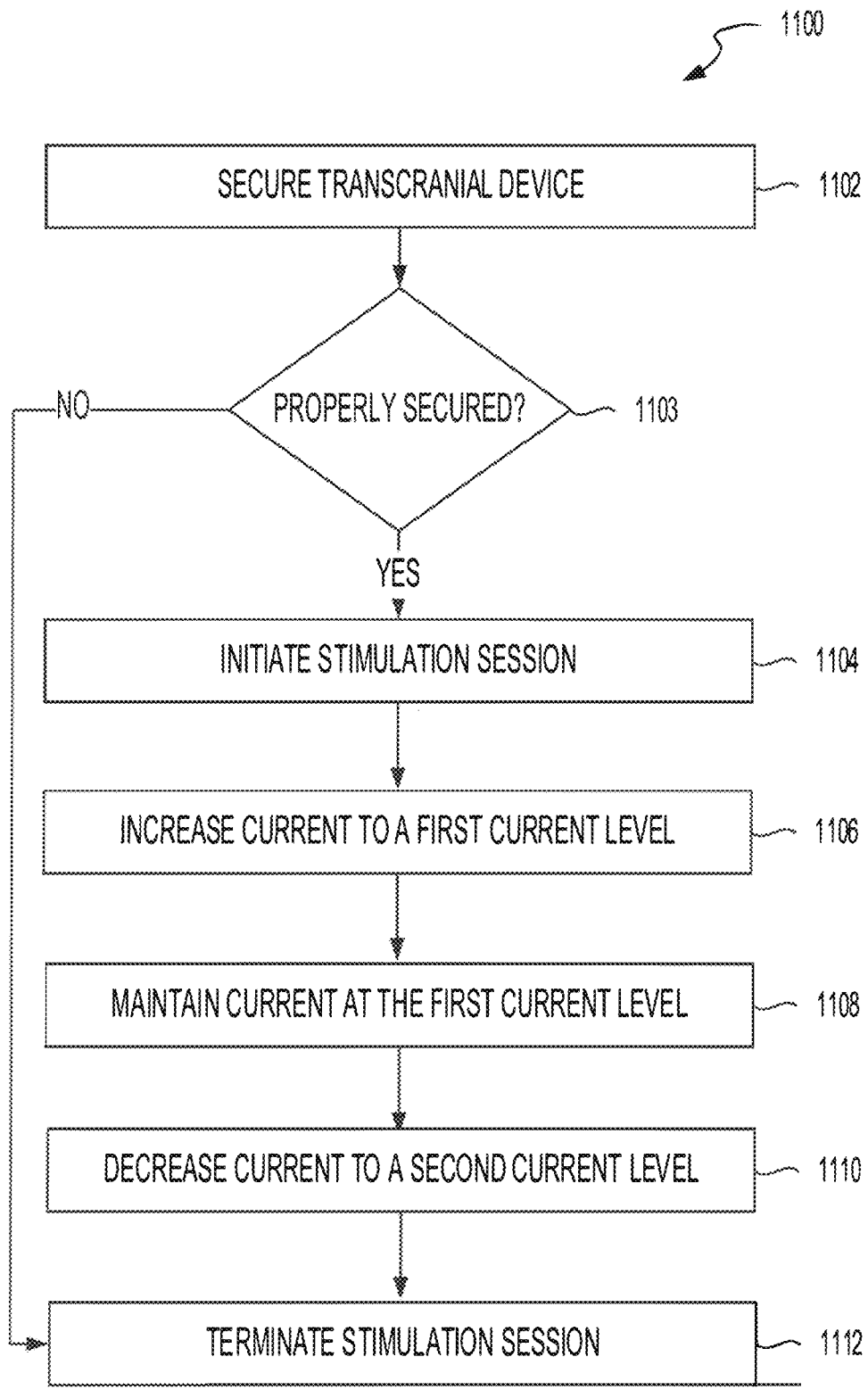
FIG. 11 illustrates a flow diagram of an example method for engaging in transcranial electrical stimulation.

Referring to FIG. 11, a flow diagram of an example method 1100 for engaging in transcranial electrical stimulation is shown. The method 1100 can include securing a transcranial electrical stimulation device to a head of a user (BLOCK 1102). The method 1100 can include confirming that the transcranial electrical stimulation device is properly secured (BLOCK 1103). The method 1100 can include initiating, by a control circuit 1102, a stimulation session (BLOCK 1104). The method 1100 can include increasing, by the control circuit 1102, a current to a first current level over a first period of time (BLOCK 1106). The method 1100 can include maintaining, by the control circuit 1102, the current at the first current level over a second period of time (BLOCK 1108). The method 1100 can include decreasing, by the control circuit 1102, responsive to a termination condition, the current to second current level over a third period of time (BLOCK 1110). The method 1100 can include terminating, by the control circuit 1102, the stimulation session (BLOCK 1112).

As set forth above, the method 1100 can include securing a transcranial electrical stimulation device to a head of a user (BLOCK 1102). Securing the transcranial electrical stimulation device 100 to the head of the user can include placing the first electrode 110 (or components coupled to the first electrode) and the second electrode 120 (or components coupled to the first electrode) flush against the forehead of the user. Also referring to FIG. 3, the strap 302 can wrap around the head of the user to secure the transcranial electrical stimulation device 100 to the head of the user. Securing the transcranial electrical stimulation device 100 to the head of the user can include adjusting the strap 302 to fit around users with different head sizes. The first electrode 110 can flex about the first post 114 so as to contour to the forehead of the user. Securing the transcranial electrical stimulation device 100 to the head of the user can include flexing the first electrode 110 about the first post 114. The second electrode 120 can flex about the second post 124 so as to contour to the forehead of the user. Securing the transcranial electrical stimulation device 100 to the head of the user can include flexing the second electrode 120 about the second post 124. Securing the transcranial electrical stimulation device 100 to the head of the user can include adjusting a first position of the first electrode 110 of the transcranial electrical stimulation device 100 and a second position of the second electrode 120 of the transcranial electrical stimulation device 100. The transcranial electrical stimulation device 100 can target various areas of the brain of the user (e.g., dorsolateral prefrontal cortex or the motor cortex). The first electrode can be in contact with a first region of the forehead of the user and the second electrode can be in contact with a second region of the forehead.

The method 1100 can include confirming that the transcranial electrical stimulation device is properly secured (BLOCK 1103). Confirming that the transcranial electrical stimulation device 100 is properly secured can include confirming that the transcranial electrical stimulation device 100 is properly secured to the head of the user. If the transcranial electrical stimulation device 100 is properly secured to the head of the user, the control circuit 1102 can initiate a stimulation session. If the transcranial electrical stimulation device 100 is improperly secured to the head of the user, the control circuit 1102 can terminate the stimulation session.

The method 1100 can include initiating, by a control circuit, a stimulation session (BLOCK 1104). Initiating, by a control circuit 1102, a stimulation session can include the control circuit 1102 coupling a power supply 1104 to a first electrode and a second electrode to enter a powered state. Initiating, by a control circuit 1102, a stimulation session can include the transcranial electrical stimulation device 100 entering a powered state. Also referring to FIG. 4, a user can press and hold the power button 402 to turn on the transcranial electrical stimulation device 100. The LED 404 can emit a blue light. The LED can flash periodically. The method 1100 can include confirming, by the LED through visual cues, that the transcranial electrical stimulation device 100 is properly secured to the head of the user. Initiating the stimulation session 1104 can occur responsive to a confirmation that the transcranial electrical stimulation device 100 is properly secured. Initiating a stimulation session can include initiating, by activating the power button 402, the stimulation session. The LED can signal an operational state of the transcranial electrical stimulation device 100. For example, an operational state can include proper placement of the transcranial electrical stimulation device 100, a stimulation session, or a current increase or a current decrease.

The method 1100 can include increasing, by the control circuit, a current to a first current level over a first period of time (BLOCK 1106). Increasing a current to a first level over a first period of time can include flowing current through the head of the user from a first electrode 110 of the transcranial electrical stimulation device 100 to a second electrode 120 of the transcranial electrical stimulation device 100. The first period of time can be between 10 seconds and 50 seconds, such as between 10 seconds and 15 seconds. The first period of time can be 30 seconds. The current can increase from 0 mA to a first current level (e.g., 1.2 mA).

The method 1100 can include maintaining, by the control circuit, the current at the first current level over a second period of time (BLOCK 1108). Maintaining the current at the first current level over a second period of time can include flowing current through the head of the user from a first electrode 110 of the transcranial electrical stimulation device 100 to a second electrode 120 of the transcranial electrical stimulation device 100. The second period of time can be 20 minutes. The first current level can be 1.2 mA. The first current level can be adjustable to achieve a higher current level. The first current level can be adjustable to achieve a lower current level. Maintaining the current level at the first current level can include maintaining the current at a constant current.

The method 1100 can include decreasing, by the control circuit, responsive to a termination condition, the current to second current level over a third period of time (BLOCK 1110). Decreasing the current to second current level over a third period of time can include flowing current through the head of the user from a first electrode 110 of the transcranial electrical stimulation device 100 to a second electrode 120 of the transcranial electrical stimulation device 100. The third period of time can be 30 seconds. The second current level can be 0 mA. The third period of time can be between 10 seconds and 50 seconds, such as between 10 seconds and 15 seconds. The second period of time can be 30 seconds. The current can decrease from first current level (e.g., 1.2 mA) to a second current level (0 mA). The termination condition can be a variety of conditions. For example, the termination condition can be a predetermined length of time (e.g., 20 minutes). The termination condition can be an interrupted stimulation session. For example, a user may want to end the stimulation session early. The user can activate the power button to decrease the current to the second current level over the third period of time. The termination condition can be met if the transcranial electrical stimulation device 100 is accidentally moved or removed from the head of the user.

The termination condition can be a resistance exceeding a threshold. For example, the termination condition can be that the resistance of the circuit exceeds a threshold of 15 kΩ. If the resistance of the circuit exceeds 15 kΩ, the control circuit 1002 can initiate a decrease of current over the third period of time. If the resistance of the resistance of the circuit is infinite, the control circuit 1002 can immediately stop the flow of current through the head of the user from the first electrode 110 of the transcranial electrical stimulation device 100 to the second electrode 120 of the transcranial electrical stimulation device 100.

The method 1100 can include terminating, by the control circuit, the stimulation session (BLOCK 1112). Terminating, by a control circuit 1002, a stimulation session can include the control circuit 1002 decoupling a power supply 1004 to the first electrode and the second electrode to exit the powered state. Terminating the stimulation session can include the transcranial electrical stimulation device 100 exiting the powered state. Terminating the stimulation session can include stopping the flow of current through the head of the user from a first electrode 110 of the transcranial electrical stimulation device 100 to a second electrode 120 of the transcranial electrical stimulation device 100. Terminating a stimulation session can include terminating, by activating the power button 402, the stimulation session.

In some embodiments, a method for engaging in transcranial electrical stimulation comprising securing a transcranial electrical stimulation device to a head of a user in a first orientation (as shown in FIG. 2H) such that a first electrode is electrically coupled and positioned proximate to a first surface region of the head and a second electrode is electrically coupled and positioned proximate to a second surface region of the head. The method includes initiating, via a control circuit, a stimulation session. The control circuit couples a power supply to the first electrode and the second electrode to enter a first powered state, increases a current to a first current level over a first period of time, wherein the current flows from the first electrode through the head of the user in a first direction to the second electrode (for instance, from the first surface region of the head to the second surface region of the head), maintains the current at the first current level over a second period of time, decreases, responsive to a termination condition, the current to a second current level over a third period of time, and terminates the stimulation session wherein the control circuit decouples the power supply to the first electrode and the second electrode to exit the powered state. The method also includes removing the transcranial electrical stimulation device from the head of the user. The method further includes securing the transcranial electrical stimulation device to the head of the user in a second orientation (as shown in FIG. 2I) such that the first electrode is electrically coupled and positioned proximate to the second surface region of the head and the second electrode is electrically coupled and positioned proximate to the first surface region of the head and initiating, via the control circuit, a second stimulation session. The control circuit couples the power supply to the first electrode and the second electrode to enter a second powered state; increases the current to the first current level over a third period of time, wherein the current flows from the first electrode through the head of the user in a second direction to the second electrode for instance, from the second surface region of the head to the first surface region of the head), maintains the current at the first current level over a fourth period of time, and decreases, responsive to a termination condition, the current to the second current level over a fifth period of time; and terminates the stimulation session, wherein the control circuit decouples the power supply to the first electrode and the second electrode to exit the powered state. The method further includes removing the transcranial electrical stimulation device from the head of the user. The first surface region of the head can be the left prefrontal cortex and the second surface region of the head can be the right prefrontal cortex or vice versa.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

What is claimed is:

1. A method for engaging in transcranial electrical stimulation comprising:
    securing a transcranial electrical stimulation device to a head of a user in a first orientation such that a first electrode is electrically coupled and positioned proximate to a first surface region of the head and a second electrode is electrically coupled and positioned proximate to a second surface region of the head;
    initiating, via a control circuit, a first stimulation session wherein the control circuit:
        couples a power supply to the first electrode and the second electrode to enter a first powered state;
        increases a current to a first current level over a first period of time, wherein the current flows from the first electrode through the head of the user in a first direction to the second electrode;
        maintains the current at the first current level over a second period of time;
        decreases, responsive to a termination condition, the current to a second current level over a third period of time; and
        terminates the first stimulation session wherein the control circuit decouples the power supply to the first electrode and the second electrode to exit the powered state;
    removing the transcranial electrical stimulation device from the head of the user;
    securing the transcranial electrical stimulation device to the head of the user in a second orientation such that the first electrode is electrically coupled and positioned proximate to the second surface region of the head and the second electrode is electrically coupled and positioned proximate to the first surface region of the head;
    initiating, via the control circuit, a second stimulation session wherein the control circuit:
        couples the power supply to the first electrode and the second electrode to enter a second powered state;
        increases the current to the first current level over a fourth period of time, wherein the current flows from the first electrode through the head of the user in a second direction to the second electrode;
        maintains the current at the first current level over a fifth period of time;
        decreases, responsive to a termination condition, the current to the second current level over a sixth period of time; and
        terminates the second stimulation session wherein the control circuit decouples the power supply to the first electrode and the second electrode to exit the powered state; and
    removing the transcranial electrical stimulation device from the head of the user.

2. The method of claim 1, wherein the transcranial electrical stimulation device comprises a light emitting diode ("LED") and the method further comprises:
    confirming, by the LED through visual cues, that the transcranial electrical stimulation device is properly secured to the head of the user; and
    wherein initiating the stimulation session occurs responsive to a confirmation that the transcranial electrical stimulation device is properly secured.

3. The method of claim 1, wherein the transcranial electrical stimulation device comprises a power button and the method comprises:
    initiating the first stimulation session responsive to activation of the power button; and
    terminating the first stimulation session responsive to activation of the power button subsequent to the initiation of the first stimulation session.

4. The method of claim 1, further comprising signaling, by an audio component, an operational state of the transcranial electrical stimulation device.

5. The method of claim 1, wherein the first period is between 10 seconds and 50 seconds.

6. The method of claim 1, wherein the second period is between 5 minutes and 60 minutes.

7. The method of claim 1, wherein the third period is between 10 seconds and 50 seconds.

8. The method of claim 1, wherein the second period is different than the fifth period.

* * * * *